United States Patent
Friesen et al.

(10) Patent No.: US 11,913,903 B1
(45) Date of Patent: Feb. 27, 2024

(54) SYSTEMS AND METHODS FOR TESTING AND MEASURING COMPOUNDS

(71) Applicant: Source Global, PBC, Scottsdale, AZ (US)

(72) Inventors: Cody Alden Friesen, Scottsdale, AZ (US); Paul Bryan Johnson, Scottsdale, AZ (US); Jonathan Edward Goldberg, Scottsdale, AZ (US); Jose Antonio Bautista Martinez, Scottsdale, AZ (US); Maya Muyurina Castro De La Torre, Scottsdale, AZ (US)

(73) Assignee: Source Global, PBC, Scottsdale, AZ (US)

( * ) Notice: Subject to any disclaimer, the term of this patent is extended or adjusted under 35 U.S.C. 154(b) by 0 days.

(21) Appl. No.: 18/108,459

(22) Filed: Feb. 10, 2023

Related U.S. Application Data

(63) Continuation of application No. 17/953,245, filed on Sep. 26, 2022, which is a continuation of application No. 16/791,895, filed on Feb. 14, 2020, now abandoned, which is a continuation of application No. PCT/US2019/057492, filed on Oct. 22, 2019, which is a continuation of application No. 16/167,295, filed on Oct. 22, 2018, now abandoned.

(51) Int. Cl.
*G01N 27/416* (2006.01)

(52) U.S. Cl.
CPC .................. *G01N 27/4166* (2013.01)

(58) Field of Classification Search
CPC .................................................. G01N 27/4166
See application file for complete search history.

(56) References Cited

U.S. PATENT DOCUMENTS

| | | | |
|---|---|---|---|
| 1,816,592 | A | 7/1931 | Knapen |
| 2,138,689 | A | 11/1938 | Altenkirch |
| 2,284,914 | A | 6/1942 | Miller |
| 2,462,952 | A | 3/1949 | Dunkak |
| 2,700,537 | A | 1/1955 | Pennington |
| 2,761,292 | A | 9/1956 | Coanda et al. |
| 3,102,532 | A | 9/1963 | Shoemaker |

(Continued)

FOREIGN PATENT DOCUMENTS

| | | |
|---|---|---|
| CN | 1592831 | 3/2005 |
| CN | 101278164 | 3/2005 |

(Continued)

OTHER PUBLICATIONS

Non-Final Office Action dated Jan. 17, 2020 in U.S. Appl. No. 15/528,366.

(Continued)

*Primary Examiner* — Joshua L Allen
*Assistant Examiner* — Shizhi Qian
(74) *Attorney, Agent, or Firm* — Snell & Wilmer L.L.P.

(57) ABSTRACT

A water testing and measuring system is disclosed including a water generator configured to generate water by extracting water vapor from ambient air. A compound generator is configured to apply a compound to the water generated by the water generator. A processor is in communication with the water generator and the compound generator. A measurement device is in communication with the water generator, the compound generator and the processor.

22 Claims, 10 Drawing Sheets

(56) References Cited

U.S. PATENT DOCUMENTS

| | | |
|---|---|---|
| 3,400,515 A | 9/1968 | Ackerman |
| 3,676,321 A * | 7/1972 | Cummings ........ G01N 33/1806 |
| | | 205/780 |
| 3,683,591 A | 8/1972 | Glav |
| 3,726,778 A | 4/1973 | Seltzer et al. |
| 3,740,959 A | 6/1973 | Foss |
| 3,844,737 A | 10/1974 | Macriss et al. |
| 3,889,532 A | 6/1975 | Pilie et al. |
| 3,889,742 A | 6/1975 | Rush et al. |
| 4,054,124 A | 10/1977 | Knoos |
| 4,080,186 A | 3/1978 | Ockert |
| 4,117,831 A | 10/1978 | Bansal et al. |
| 4,134,743 A | 1/1979 | Macriss et al. |
| 4,136,672 A | 1/1979 | Hallanger |
| 4,146,372 A | 3/1979 | Groth et al. |
| 4,169,459 A | 10/1979 | Ehrlich |
| 4,185,969 A | 1/1980 | Bulang |
| 4,201,195 A | 5/1980 | Sakhuja |
| 4,219,341 A | 8/1980 | Hussmann |
| 4,222,244 A | 9/1980 | Meckler |
| 4,234,037 A | 11/1980 | Rogers et al. |
| 4,242,112 A | 12/1980 | Jebens |
| 4,285,702 A | 8/1981 | Michel et al. |
| 4,304,577 A | 12/1981 | Ito et al. |
| 4,315,599 A | 2/1982 | Biancardi |
| 4,334,524 A | 6/1982 | McCullough |
| 4,342,569 A | 8/1982 | Hussmann |
| 4,345,917 A | 8/1982 | Hussmann |
| 4,351,651 A | 9/1982 | Courneya |
| 4,374,655 A | 2/1983 | Grodzka et al. |
| 4,377,398 A | 3/1983 | Bennett |
| 4,398,927 A | 8/1983 | Asher et al. |
| 4,405,343 A | 9/1983 | Othmer |
| 4,433,552 A | 2/1984 | Smith |
| 4,478,210 A | 10/1984 | Sieradski |
| 4,722,192 A | 2/1988 | Koblitz et al. |
| 4,726,817 A | 2/1988 | Roger |
| 4,926,618 A | 5/1990 | Ratliff |
| 5,058,388 A | 10/1991 | Shaw et al. |
| 5,123,777 A | 6/1992 | Tadros |
| 5,148,374 A | 9/1992 | Coellner |
| 5,213,773 A | 5/1993 | Burris |
| 5,275,643 A | 1/1994 | Usui |
| 5,399,247 A * | 3/1995 | Carey ................ C02F 1/46109 |
| | | 205/688 |
| 5,470,484 A | 11/1995 | McNeel |
| 5,579,647 A | 12/1996 | Calton et al. |
| 5,701,749 A | 12/1997 | Zakryk |
| 5,718,122 A | 2/1998 | Maeda |
| 5,729,981 A | 3/1998 | Markus et al. |
| 5,758,508 A | 6/1998 | Belding et al. |
| 5,758,511 A | 6/1998 | Yoho et al. |
| 5,826,434 A | 10/1998 | Belding et al. |
| 5,846,296 A | 12/1998 | Krumsvik |
| 5,873,256 A | 2/1999 | Denniston |
| 5,989,313 A | 11/1999 | Mize |
| 6,029,467 A | 2/2000 | Moratalla |
| 6,156,102 A | 12/2000 | Contad et al. |
| 6,199,388 B1 | 3/2001 | Fischer, Jr. |
| 6,336,957 B1 | 1/2002 | Tsymerman |
| 6,447,583 B1 | 9/2002 | Thelen et al. |
| 6,490,879 B2 | 12/2002 | Lloyd et al. |
| 6,511,525 B2 | 1/2003 | Spletzer et al. |
| 6,513,339 B1 | 2/2003 | Kopko |
| 6,557,365 B2 | 5/2003 | Dinnage et al. |
| 6,574,979 B2 | 6/2003 | Faqih |
| 6,644,060 B1 | 11/2003 | Dagan |
| 6,828,499 B2 | 12/2004 | Max |
| 6,869,464 B2 | 3/2005 | Klemic |
| 6,945,063 B2 | 9/2005 | Max |
| 6,957,543 B1 | 10/2005 | Reznik |
| 7,017,356 B2 | 3/2006 | Moffitt |
| 7,043,934 B2 | 5/2006 | Radermacher et al. |
| 7,178,355 B2 | 2/2007 | Moffitt |
| 7,251,945 B2 | 8/2007 | Tongue |
| 7,305,849 B2 | 12/2007 | Loffler et al. |
| 7,306,654 B2 | 12/2007 | King et al. |
| 7,478,535 B2 | 1/2009 | Turner, Jr. et al. |
| 7,740,765 B2 | 6/2010 | Mitchell |
| 7,866,176 B2 | 1/2011 | Vetrovec et al. |
| 7,905,097 B1 | 3/2011 | Fort |
| 7,926,481 B2 | 4/2011 | Edwards et al. |
| 8,075,652 B2 | 12/2011 | Melikyan |
| 8,118,912 B2 | 2/2012 | Rodriguez et al. |
| 8,187,368 B2 | 5/2012 | Shih |
| 8,196,422 B2 | 6/2012 | Ritchey |
| 8,328,904 B2 | 12/2012 | Griffiths et al. |
| 8,425,660 B2 | 4/2013 | Ike et al. |
| 8,506,675 B2 | 8/2013 | Ellsworth |
| 8,844,299 B2 | 9/2014 | Ferreira et al. |
| 8,876,956 B2 | 11/2014 | Ball et al. |
| 9,289,718 B2 | 3/2016 | Dahlback |
| 10,357,739 B2 | 7/2019 | Friesen et al. |
| 10,469,028 B2 | 11/2019 | Friesen et al. |
| 10,632,416 B2 | 4/2020 | Friesen et al. |
| 10,835,861 B2 | 11/2020 | Friesen et al. |
| 11,159,123 B2 | 10/2021 | Friesen et al. |
| 11,160,223 B2 | 11/2021 | Friesen et al. |
| 11,266,944 B2 | 3/2022 | Friesen et al. |
| 11,281,997 B2 | 3/2022 | Friesen et al. |
| 11,285,435 B2 | 3/2022 | Friesen et al. |
| 11,359,356 B2 | 6/2022 | Friesen et al. |
| 11,384,517 B2 | 7/2022 | Friesen et al. |
| 11,414,843 B2 | 8/2022 | Friesen et al. |
| 11,447,407 B2 | 9/2022 | Friesen et al. |
| 11,555,421 B2 | 1/2023 | Friesen et al. |
| 2002/0130091 A1 | 9/2002 | Ekberg et al. |
| 2003/0091881 A1 | 5/2003 | Eisler |
| 2003/0101161 A1 | 5/2003 | Ferguson et al. |
| 2004/0000165 A1 | 1/2004 | Max |
| 2004/0055309 A1 | 3/2004 | Bellows et al. |
| 2005/0044862 A1 | 3/2005 | Vetrovec et al. |
| 2005/0084415 A1 | 4/2005 | McVey et al. |
| 2005/0204914 A1 | 9/2005 | Boutall |
| 2005/0226774 A1 * | 10/2005 | Kounaves .......... G01N 33/1846 |
| | | 422/68.1 |
| 2005/0249631 A1 | 11/2005 | Schulz et al. |
| 2005/0284167 A1 | 12/2005 | Morgan |
| 2006/0017740 A1 | 1/2006 | Coleman |
| 2006/0032493 A1 | 2/2006 | Ritchey |
| 2006/0060475 A1 | 3/2006 | Applegate et al. |
| 2006/0112709 A1 | 6/2006 | Boyle |
| 2006/0130654 A1 | 6/2006 | King et al. |
| 2006/0288709 A1 | 12/2006 | Reidy |
| 2007/0028769 A1 | 2/2007 | Eplee et al. |
| 2007/0101862 A1 | 5/2007 | Tongue |
| 2007/0150424 A1 | 6/2007 | Igelnik |
| 2007/0274858 A1 | 11/2007 | Childers et al. |
| 2007/0295021 A1 | 12/2007 | Tyls et al. |
| 2008/0135495 A1 | 6/2008 | Sher |
| 2008/0168789 A1 | 7/2008 | Jones |
| 2008/0202944 A1 | 8/2008 | Santoli et al. |
| 2008/0224652 A1 | 9/2008 | Zhu et al. |
| 2008/0245092 A1 | 10/2008 | Forsberg et al. |
| 2008/0289352 A1 | 11/2008 | Parent |
| 2009/0025711 A1 | 1/2009 | Edwards et al. |
| 2009/0093916 A1 | 4/2009 | Parsonnet et al. |
| 2009/0173376 A1 | 7/2009 | Spencer et al. |
| 2009/0211276 A1 | 8/2009 | Forkosh |
| 2009/0223236 A1 | 9/2009 | Call et al. |
| 2009/0223514 A1 | 9/2009 | Smith et al. |
| 2010/0083673 A1 | 4/2010 | Meritt |
| 2010/0170499 A1 | 7/2010 | Bar |
| 2010/0192605 A1 | 8/2010 | Fang et al. |
| 2010/0212348 A1 | 8/2010 | Oh |
| 2010/0242507 A1 | 9/2010 | Meckler |
| 2010/0275263 A1 | 11/2010 | Erickson |
| 2010/0275775 A1 | 11/2010 | Griffiths et al. |
| 2010/0294672 A1 * | 11/2010 | Gahr ..................... G01N 27/42 |
| | | 205/786 |
| 2010/0300868 A1 | 12/2010 | Pirone |
| 2011/0048039 A1 | 3/2011 | Kohavi et al. |
| 2011/0056220 A1 | 3/2011 | Caggiano |
| 2011/0083458 A1 | 4/2011 | Takakura et al. |

(56) References Cited

U.S. PATENT DOCUMENTS

| | | | |
|---|---|---|---|
| 2011/0132027 A1 | 6/2011 | Gommed et al. |
| 2011/0232485 A1 | 9/2011 | Ellsworth |
| 2011/0247353 A1 | 10/2011 | Metz |
| 2011/0296858 A1 | 12/2011 | Caggiano |
| 2012/0006193 A1 | 1/2012 | Roychoudhury |
| 2012/0125020 A1 | 5/2012 | Vandermeulen et al. |
| 2012/0227582 A1 | 9/2012 | Wamstad et al. |
| 2012/0323098 A1 | 12/2012 | Moein et al. |
| 2013/0227879 A1 | 9/2013 | Lehky |
| 2013/0269522 A1 | 10/2013 | DeValve |
| 2013/0312451 A1 | 11/2013 | Max |
| 2013/0318790 A1 | 12/2013 | Becze et al. |
| 2013/0319022 A1 | 12/2013 | Becze et al. |
| 2014/0034475 A1 | 2/2014 | Kamen et al. |
| 2014/0053580 A1 | 2/2014 | Ferreira et al. |
| 2014/0110273 A1 | 4/2014 | Bar-or et al. |
| 2014/0138236 A1 | 5/2014 | White |
| 2014/0157985 A1 | 6/2014 | Scovazzo et al. |
| 2014/0173769 A1 | 6/2014 | Leyns et al. |
| 2014/0260389 A1 | 9/2014 | Sistla |
| 2014/0317029 A1 | 10/2014 | Matsuoka et al. |
| 2015/0033774 A1 | 2/2015 | Ferreira et al. |
| 2015/0136666 A1 | 5/2015 | Zamir et al. |
| 2015/0194926 A1 | 7/2015 | Bushong, Jr. |
| 2015/0226697 A1* | 8/2015 | Morgan .............. G01N 27/4168 |
| | | | 204/402 |
| 2016/0073589 A1 | 3/2016 | McNamara |
| 2016/0131401 A1 | 5/2016 | Otanicar et al. |
| 2016/0162456 A1 | 6/2016 | Munro et al. |
| 2016/0187287 A1* | 6/2016 | Tajiri ..................... G01N 33/18 |
| | | | 205/775.5 |
| 2016/0197364 A1 | 7/2016 | Rama |
| 2016/0209346 A1 | 7/2016 | Brondum et al. |
| 2016/0244951 A1 | 8/2016 | Yui |
| 2016/0333553 A1 | 11/2016 | Dorfman |
| 2017/0013810 A1 | 1/2017 | Grabell |
| 2017/0024641 A1 | 1/2017 | Wierzynski |
| 2017/0203974 A1 | 7/2017 | Riedl et al. |
| 2017/0323221 A1 | 11/2017 | Chaudhuri et al. |
| 2017/0354920 A1 | 12/2017 | Friesen et al. |
| 2017/0371544 A1 | 12/2017 | Choi et al. |
| 2018/0043295 A1 | 2/2018 | Friesen et al. |
| 2018/0209123 A1 | 7/2018 | Bahrami et al. |
| 2018/0369713 A1* | 12/2018 | Dorfman ................ B01D 5/006 |
| 2019/0025273 A1* | 1/2019 | Brondum ................ G01N 27/07 |
| 2019/0102695 A1 | 4/2019 | Biswas et al. |
| 2019/0171967 A1 | 6/2019 | Friesen et al. |
| 2019/0254243 A1 | 8/2019 | Friesen et al. |
| 2019/0336907 A1 | 11/2019 | Friesen et al. |
| 2019/0344214 A1 | 11/2019 | Friesen et al. |
| 2019/0372520 A1 | 12/2019 | Friesen et al. |
| 2020/0049682 A1 | 2/2020 | Fukuzawa et al. |
| 2020/0055753 A1 | 2/2020 | Minor et al. |
| 2020/0122083 A1 | 4/2020 | Friesen et al. |
| 2020/0124566 A1 | 4/2020 | Johnson et al. |
| 2020/0140299 A1 | 5/2020 | Friesen et al. |
| 2020/0209190 A1* | 7/2020 | Johnson ............. G01N 27/4167 |
| 2020/0269184 A1 | 8/2020 | Friesen et al. |
| 2020/0283997 A1 | 9/2020 | Salloum et al. |
| 2020/0286997 A1 | 9/2020 | Wu et al. |
| 2020/0300128 A1 | 9/2020 | Friesen et al. |
| 2020/0361965 A1 | 11/2020 | Yaghi et al. |
| 2021/0062478 A1 | 3/2021 | Friesen et al. |
| 2021/0192368 A1 | 6/2021 | Schall |
| 2021/0305935 A1 | 9/2021 | Friesen et al. |
| 2022/0039341 A1 | 2/2022 | Friesen et al. |
| 2022/0127172 A1 | 4/2022 | Friesen et al. |
| 2022/0136270 A1 | 5/2022 | Gamboa et al. |
| 2022/0156648 A1 | 5/2022 | Friesen et al. |
| 2022/0176314 A1 | 6/2022 | Friesen et al. |
| 2022/0228351 A1 | 7/2022 | Friesen et al. |
| 2022/0259838 A1 | 8/2022 | Friesen et al. |
| 2022/0274048 A1 | 9/2022 | Friesen et al. |
| 2022/0307240 A1 | 9/2022 | Friesen et al. |
| 2022/0316192 A1 | 10/2022 | Friesen et al. |
| 2022/0341134 A1 | 10/2022 | Friesen et al. |
| 2022/0411297 A1 | 12/2022 | Friesen et al. |
| 2023/0014032 A1 | 1/2023 | Friesen et al. |
| 2023/0078132 A1 | 3/2023 | Friesen et al. |
| 2023/0113840 A1 | 4/2023 | Friesen et al. |
| 2023/0130872 A1 | 4/2023 | Friesen et al. |

FOREIGN PATENT DOCUMENTS

| | | |
|---|---|---|
| CN | 1774401 | 5/2006 |
| CN | 101589282 | 11/2009 |
| CN | 102042645 | 5/2011 |
| CN | 102297503 | 12/2011 |
| CN | 102422089 | 4/2012 |
| CN | 102441320 | 5/2012 |
| CN | 102733451 | 10/2012 |
| CN | 202850099 | 4/2013 |
| CN | 103889892 | 6/2014 |
| CN | 203777907 | 8/2014 |
| CN | 104813107 | 7/2015 |
| CN | 204510348 U | 7/2015 |
| CN | 105531547 | 4/2016 |
| CN | 107447811 | 12/2017 |
| DE | 4215839 | 11/1993 |
| EP | 1139554 | 10/2001 |
| EP | 2305362 | 4/2011 |
| EP | 2326890 | 6/2011 |
| FR | 2813087 | 2/2002 |
| GB | 2237387 | 5/1991 |
| JP | H06142434 | 5/1994 |
| JP | H09-285412 | 11/1997 |
| JP | 2002-126641 | 5/2002 |
| JP | 2003-148786 | 5/2003 |
| JP | 2004-239541 | 8/2004 |
| JP | 3850498 | 11/2006 |
| JP | 2012101169 | 5/2012 |
| KR | 20000003525 | 2/2000 |
| WO | 1999007951 | 2/1999 |
| WO | 2006129200 | 12/2006 |
| WO | 2007041804 | 4/2007 |
| WO | 2007051886 | 5/2007 |
| WO | 2008018071 | 2/2008 |
| WO | 2009043413 | 4/2009 |
| WO | 2011150081 | 12/2011 |
| WO | 2012009024 | 1/2012 |
| WO | 2012128619 | 9/2012 |
| WO | 2012162760 | 12/2012 |
| WO | 2013026126 | 2/2013 |
| WO | 2013182911 | 12/2013 |
| WO | 2014085860 | 6/2014 |
| WO | 2015054435 | 4/2015 |
| WO | 2016053162 | 4/2016 |
| WO | 2016081863 | 5/2016 |
| WO | 2016138075 | 9/2016 |
| WO | 2016187709 | 12/2016 |
| WO | 2017177143 | 10/2017 |
| WO | 2017201405 | 11/2017 |
| WO | 2018013161 | 1/2018 |
| WO | 2019014599 | 1/2019 |
| WO | 2019050861 | 3/2019 |
| WO | 2019050866 | 3/2019 |
| WO | 2019071202 | 4/2019 |
| WO | 2019113354 | 6/2019 |
| WO | 2019161339 | 8/2019 |
| WO | 2019217974 | 11/2019 |
| WO | 2020082038 | 4/2020 |
| WO | 2020086621 | 4/2020 |
| WO | 2020219604 | 4/2020 |
| WO | 2021154739 | 8/2021 |
| WO | 2022093999 | 5/2022 |

OTHER PUBLICATIONS

Final Office Action dated Apr. 27, 2020 in U.S. Appl. No. 15/528,366.
Notice of Allowance dated Jun. 19, 2020 in U.S. Appl. No. 15/528,366.
Notice of Allowance dated Jun. 3, 2019 in U.S. Appl. No. 15/600,046.

(56) References Cited

OTHER PUBLICATIONS

Non-Final Office Action dated Feb. 5, 2019 in U.S. Appl. No. 15/482,104.
Notice of Allowance dated Jun. 27, 2019 in U.S. Appl. No. 15/482,104.
Non-Final Office Action dated Jun. 1, 2020 in U.S. Appl. No. 16/167,295.
Final Office Action dated Apr. 13, 2021 in U.S. Appl. No. 16/167,295.
Non-Final Office Action dated Apr. 30, 2021 in U.S. Appl. No. 16/278,608.
Non-Final Office Action dated Jul. 20, 2021 in U.S. Appl. No. 16/211,896.
Notice of Allowance dated Nov. 10, 2021 in U.S. Appl. No. 16/211,896.
Non-Final Office Action dated May 11, 2022 in U.S. Appl. No. 16/411,048.
Notice of Allowance dated Oct. 20, 2022 in U.S. Appl. No. 16/411,048.
Non-Final Office Action dated Aug. 9, 2019 in U.S. Appl. No. 16/517,435.
Notice of Allowance dated Jan. 31, 2020 in U.S. Appl. No. 16/517,435.
Non-Final Office Action dated Jul. 26, 2021 in U.S. Appl. No. 16/630,824.
Final Office Action dated Jan. 11, 2022 in U.S. Appl. No. 16/630,824.
Non-Final Office Action dated Mar. 2, 2022 in U.S. Appl. No. 16/630,824.
Notice of Allowance dated Aug. 3, 2022 in U.S. Appl. No. 16/630,824.
Notice of Allowance dated Feb. 4, 2022 in U.S. Appl. No. 16/644,465.
Notice of Allowance dated Mar. 7, 2022 in U.S. Appl. No. 16/644,487.
Non-Final Office Action dated Aug. 24, 2021 in U.S. Appl. No. 16/657,935.
Non-Final Office Action dated Apr. 12, 2022 in U.S. Appl. No. 16/753,560.
Notice of Allowance dated Sep. 14, 2022 in U.S. Appl. No. 16/753,560.
Non-Final Office Action dated May 15, 2020 in U.S. Appl. No. 16/791,895.
Final Office Action dated Oct. 15, 2020 in U.S. Appl. No. 16/791,895.
Non-Final Office Action dated Jun. 8, 2021 in U.S. Appl. No. 16/791,895.
Final Office Action dated Dec. 20, 2021 in U.S. Appl. No. 16/791,895.
Non Final Office Action dated Jun. 24, 2022 in U.S. Appl. No. 16/791,895.
Notice of Allowance dated Oct. 20, 2021 in U.S. Appl. No. 16/820,587.
Non-Final Office Action dated May 6, 2022 in U.S. Appl. No. 16/855,965.
Non-Final Office Action dated Sep. 15, 2022 in U.S. Appl. No. 17/081,898.
Notice of Allowance dated Sep. 15, 2022 in U.S. Appl. No. 17/081,898.
Office Action dated Apr. 10, 2023 in U.S. Appl. No. 17/859,971.
Non-Final Office Action dated Mar. 2, 2023 in U.S. Appl. No. 17/899,416.
Non-Final Office Action dated Mar. 29, 2023 in U.S. Appl. No. 17/832,977.
International Search Report and Written Opinion dated Apr. 29, 2016 in Application No. PCT/US2015/061921.
International Search Report and Written Opinion in Aug. 16, 2017 in Application No. PCT/US2017/033540.
International Search Report and Written Opinion dated Jun. 19, 2017 in Application No. PCT/US2017/026609.
International Search Report and Written Opinion dated Dec. 3, 2018 in Application No. PCT/US2018/049411.
International Search Report and Written Opinion dated Dec. 3, 2018. Application No. PCT/US2018/049398.
International Search Report and Written Opinion dated Jan. 15, 2019 in Application No. PCT/US2018/054715.
International Search Report and Written Opinion dated Mar. 6, 2019 in Application No. PCT/US2018/042098.
International Search Report and Written Opinion dated Mar. 29, 2019 in Application No. PCT/US2018/064308.
International Search Report and Written Opinion dated Jun. 6, 2019 in Application No. PCT/US2019/018431.
International Search Report and Written Opinion dated Jul. 29, 2019 in Application No. PCT/US2019/32066.
International Search Report and Written Opinion dated Jan. 28, 2020 in Application No. PCT/US2019/057492.
International Search Report and Written Opinion dated Mar. 19, 2020 in Application No. PCT/US2019/057081.
International Search Report and Written Opinion dated Jun. 15, 2020 in Application No. PCT/US2020/029401.
International Search Report and Written Opinion dated Apr. 6, 2021 in Application No. PCT/US2021/015106.
International Search Report and Written Opinion dated Feb. 16, 2022 in Application No. PCT/US2021/056910.
International Search Report and Written Opinion dated May 11, 2022 in Application No. PCT/US2022/012909.
European Search Report dated Jun. 7, 2019 in European Application No. 15825979.
European Search Report dated Jan. 28, 2020 in European Application No. 15825979.
Office Action dated Oct. 31, 2019 in Chinese Application No. 201780033378.3.
Office Action dated Apr. 6, 2021 in Chinese Application No. 201780033378.3.
Office Action dated Aug. 4, 2021 in Chinese Application No. 201780033378.3.
Office Action dated Nov. 1, 2021 in Chinese Application No. 201780033378.3.
Office Action dated Feb. 4, 2020 in Brazilian Patent Application No. 112017021842.9.
Office Action dated Jul. 15, 2021 in Japanese Patent Application No. 2019-503636.
Office Action dated Apr. 28, 2021 in India Patent Application No. 20181704169.
Office Action dated Jul. 29, 2021 in India Patent Application No. 202017005710.
Office Action dated Mar. 1, 2022 in India Patent Application No. 202017014752.
Office Action dated Oct. 31, 2022 in India Patent Application No. 202117022077.
Office Action dated Mar. 6, 2023 in India Patent Application No. 202017037089.
Office Action dated Oct. 10, 2022 in Chinese Patent Application No. 202110545596.3.
Office Action dated May 5, 2023 in Chinese Patent Application No. 201780044144.9.
Ali et al., "Desiccant Enhanced Nocturnal Radiative Cooling-Solar Collector System for Air Comfort Application in Hot Arid Areas," Int. J. of Thermal & Environmental Engineering, vol. 5, No. 1, pp. 71-82 (2013).
Anand et al., "Solar Cooling Systems for Climate Change Mitigation: A Review," Renewable and Sustainable Energy Reviews , vol. 41, pp. 143-161 (2015).
De Antonellis et al., "Simulation, Performance Analysis and Optimization of Desiccant Wheels," Energy and Buildings, vol. 42, No. 9, pp. 1386-1393 (2010).
Eriksson et al., "Diurnal Variations of Humidity and Ice Water Content in the Tropical Upper Troposphere," Atmos. Chem. Phys,. vol. 10, pp. 11519-11533 (2010).
European Solar Thermal Industry Federation (ESTIF), "Key Issues for Renewable Heat in Europe (K4RES-H)," Solar Assisted Cooling-WP3, Task 3.5, Contract EIE/04/204/S07.38607, pp. 1-21 (2006).
Ge et al., "A Mathematical Model for Predicting the Performance of a Compound Desiccant Wheel (A Model of a Compound Desiccant Wheel)," Applied Thermal Engineering, vol. 30, No. 8, pp. 1005-1015 (2010).
Kassem et al., "Solar Powered Dehumidification Systems Using Desert Evaporative Coolers: Review," International Journal of Engineering and Advanced Technology {IJEAT), ISSN: 2249-8958, vol. 3, Issue 1 (2013).

(56) References Cited

OTHER PUBLICATIONS

Kolewar et al., "Feasability of Solar Desiccant Evaporative Cooling: A Review," International Journal of Scientific & Engineering Research, ISSN: 2229-5518, vol. 5, Issue 10 (2014).

La et al., "Technical Development of Rotary Desiccant Dehumidification and Air Conditioning: A Review," Renewable and Sustainable Energy Reviews, vol. 14, pp. 130-147 (2010).

Nia et al., "Modeling and Simulation of Desiccant Wheel for Air Conditioning," Energy and Buildings, vol. 38, No. 10, pp. 1230-1239 (2006).

Kozubal et al., "Desiccant Enhanced Evaporative Air-Conditioning {DEVap): Evaluation of a New Concept in Ultra Efficient Air Conditioning," National Renewal Energy Laboratory {NREL), Technical Report, NREL/TP-5500-49722 (2011).

Critoph et al., "Solar Energy for Cooling and Refrigeration," Engineering Department, University of Warwick, Coventry CV4 7AL, United Kingdom (1997).

Wahlgren, "Atmospheric Water Vapour Processor Designs for Potable Water Production: A Review," Wat. Res., vol. 35, No. 1, pp. 1-22 (2001).

Gad et al., "Application of a Solar Desiccant/Collector System for Water Recovery From Atmospheric Air," Renewal Energy, vol. 22, No. 4, pp. 541-556 (2001).

William et al., "Desiccant System for Water Production From Humid Air Using Solar Energy," Energy, vol. 90, pp. 1707-1720 (2015).

PV Performance Modeling Collaborative. (2014). Irradiance & Insolation. Accessed Aug. 18, 2021 at https://pvpmc.sandia.gov/modeling-steps/1-weather-design-inputs/irradiance-and-insolation-2/ (Year: 2014).

ACS. (2012). A Single-Layer Atmosphere Model. Accessed on Aug. 17, 2021 at https://www.acs.org/content/acs/en/ climatescience/atmosphericwarming/singlelayermodel.html (Year: 2012).

Materials Technology. (2010). UV Exposure Across Surface of Earth. Accessed Aug. 17, 2021 at http://www.drb-mattech.co.uk/uv%20map.html (Year: 2010).

Notice of Allowance dated Jul. 7, 2023 in U.S. Appl. No. 17/578,854.

Non-Final Office Action dated Jun. 21, 2023 in U.S. Appl. No. 17/666,442.

Non-Final Office Action dated Jun. 7, 2023 in U.S. Appl. No. 17/677,817.

Office Action dated Jan. 2, 2023 in India Patent Application No. 202117022031.

Office Action dated Jun. 1, 2023 in Chinese Patent Applciation No. 202080030614.8.

Office Action dated May 17, 2023 in European Patent Application No. 19802405.1.

Office Action dated Jun. 6, 20233 in European Patent Application No. 21747270.3.

Gentile et al., "Water production from the atmosphere in arid climates using low grade solar heat", IEA SHC International Conference on Solar Heating and Cooling for Buildings and Industry, pp. 1-12 (2017).

Kim, "Development of Adsorption-based Atmospheric Water Harvesting and Thermal Energy Storage Technologies", Massachusetts Institute of Technology, pp. 1-146 (2018).

Verougstraete et al., "A New Honeycomb Carbon Monolith for CO2 Capture by Rapid Temperature Swing Adsorption Using Steam Regeneration", Chemical Engineering Journal 383 (2020).

\* cited by examiner

SYSTEMS AND METHODS FOR TESTING AND MEASURING COMPOUNDS

BACKGROUND

Oxidizers (also referred to "oxidizing agents" or "oxidizing compounds") can be used to sanitize drinking water. In doing so, it is important to effectively measure the concentration of the oxidizing compounds to ensure both that a sufficient amount of the oxidizing compounds can be applied to sterilize the water, and that the water is safe for consumption.

Conventional apparatuses for making these measurements are plagued with various deficiencies. One deficiency is that the lifetime and reliability of these apparatuses are limited, thus requiring the measurement apparatuses to be replaced over relatively short periods of time. This deficiency can be attributed, at least in part, to the fact that these apparatuses typically rely on reference electrodes that rapidly lose chloride salts as a result of diffusion processes that take place while the reference electrodes are immersed in test fluids with the oxidizing compounds. This diffusion of salts from the reference electrodes reduces the lifetime of the reference electrodes, affects the reliability of the measurement apparatuses, and often causes failures of the measurement apparatuses. This deficiency can also be attributed, in part, to the structure of the conventional apparatus, which is composed of a Ag/AgCl probe having a junction that is susceptible to clogging, poisoning, and mechanical damage.

Provided herein are improved devices, systems, and methods for measuring oxidizing compounds in test fluids. In contrast to conventional measurement devices, the improved measurement device utilizes electrolysis to detect and measure oxidizing compounds in the test fluids.

SUMMARY

As disclosed herein, a measurement device may comprise a processor, a power supply configured to provide a constant current, a first electrode, a second electrode, and a third electrode. In various embodiments, the first electrode and the second electrode are assembled on a first circuit as a first electrode pair to which the constant current is applied, the third electrode is not assembled on the first circuit, the first electrode pair is configured to electrolyze a test fluid and measure a reference voltage indicating an electrochemical potential at which electrolysis occurs in the test fluid, the third electrode is coupled to the first electrode, and the third electrode is configured to measure a voltage indicating an oxidizing potential of the test fluid.

In various embodiments, the measurement device further comprises a temperature measurement component configured to measure a third voltage indicating a temperature of the test fluid. In various embodiments, the first electrode, the second electrode, and the third electrode each comprise at least one of a noble metal, a passivated transition metal, and a glass-like carbon. In various embodiments, the first electrode, the second electrode and the third electrode are constructed of at least one of gold, platinum, titanium, or a glass-like carbon. In various embodiments, at least one of the first electrode, the second electrode, and the third electrode comprises at least one of a pH electrode, a proton selective electrode, and an ion selective electrode. In various embodiments, the measurement device further comprises a fourth electrode assembled on a second circuit with the third electrode as a second electrode pair, wherein the second electrode pair is configured to electrolyze the test fluid and measure a voltage indicating an electrochemical potential at which electrolysis occurs in the test fluid.

In various embodiments, a system comprises a test fluid comprising a concentration of an oxidizing compound, and a measurement device. In various embodiments, the measurement device is configured to apply a constant current to the test fluid, measure a reference voltage indicating an electrochemical potential at which electrolysis occurs in the test fluid, measure a first voltage indicating a first oxidizing potential of the test fluid, compare the reference voltage to the first voltage to determine a first voltage difference, measure a second voltage indicating a second oxidizing potential of the test fluid, compare the reference voltage to the second voltage to determine a second voltage difference, and calculate the concentration of the oxidizing compound in the test fluid based on the first voltage difference and the second voltage difference.

In various embodiments, the test fluid comprises water, the oxidizing compound comprises ozone, the reference voltage indicates the electrochemical potential at which water electrolysis occurs in the water, and the oxidizing compound is ozone. In various embodiments, the measurement device is further configured to measure the pH of the test fluid. In various embodiments, the measurement device is further configured to measure an ion concentration of the test fluid.

In various embodiments, the measurement device comprises a processor, a power supply configured to apply a constant current, and a first electrode, a second electrode, and a third electrode. In various embodiments, the first electrode and the second electrode are assembled on a first circuit to which the constant current is applied when the first electrode and the second electrode are submerged in the test fluid, and the third electrode is not assembled on the first circuit, the first electrode is configured to measure the reference voltage, and the third electrode is configured to measure the first voltage and the second voltage.

In various embodiments, the first electrode, the second electrode, and the third electrode are each comprised of at least one of a noble metal, a passivated transition metal, and a glass-like carbon. In various embodiments, the measurement device further comprises a fourth electrode assembled on a second circuit with the third electrode as a second electrode pair, wherein the second electrode pair is configured to electrolyze the test fluid and measure a voltage indicating an electrochemical potential at which electrolysis occurs in the test fluid.

In various embodiments, the measurement device is configured to operate in a reverse polarization mode during which the constant current applied to the first circuit is reversed. In various embodiments, the measurement device further comprises a temperature measurement component configured to measure a third voltage indicating a temperature of the test fluid. In various embodiments, the measurement device further comprises an oxidizer generator configured to communicate the oxidizing compound to the test fluid, wherein the processor receives at least three of the reference voltage, the first voltage, the second voltage, and the third voltage, and wherein the processor controls the oxidizer generator based on the at least three of the reference voltage, the first voltage, the second voltage, and the third voltage.

In various embodiments, a method for measuring an oxidizer concentration of a test fluid comprises submerging a first electrode, a second electrode, and a third electrode of a measurement device into the test fluid. In various embodiments, the measurement device comprises a processor, a power supply that is configured to provide the constant current, and the first electrode, the second electrode, and the third electrode, wherein the first electrode and the second electrode are assembled on a first circuit to which the constant current is applied when the first electrode and the second electrode are submerged in the test fluid, the third electrode is not assembled on the circuit, and the first electrode, the second electrode, and the third electrode are each comprised of at least one of a noble metal, a passivated transition metal, a glass-like carbon, or some combination thereof.

In various embodiments, the method further comprises applying, by the power supply, a constant current to the test fluid, measuring, by at least one of the first electrode and the second electrode, a reference voltage indicating an electrochemical potential at which electrolysis occurs in the test fluid, measuring, by the third electrode, a first voltage indicating an oxidizing potential of the test fluid, and calculating, by the processor, the oxidizer concentration of the test fluid.

In various embodiments, the test fluid comprises water, the oxidizing compound comprises ozone, the reference voltage indicates the electrochemical potential at which water electrolysis occurs in the water, and the oxidizer concentration comprises an ozone concentration. In various embodiments, the method further comprises measuring, by the measurement device, the pH of the test fluid. In various embodiments, the method further comprises measuring, by the measurement device, the ion concentration of the test fluid. In various embodiments, the method further comprises operating the measurement device in reverse polarization mode.

In various embodiments, the method further comprises submerging a fourth electrode of the measurement device into the test fluid, measuring, by at least one of the third electrode and the fourth electrode, a reference voltage, measuring, by the second electrode, a second voltage indicating the oxidizing potential of the test fluid, and calculating, by the processor, the oxidizer concentration of the test fluid.

In various embodiments, the method further comprises measuring, by a temperature measurement component, a third voltage indicating a temperature of the test fluid, receiving, by the processor, the reference voltage, the first voltage, and the third voltage, and controlling, by the processor, an oxidizer generator based on the reference voltage, the first voltage, and the third voltage. In various embodiments, the method further comprises connecting the third electrode to an electrical ground, disconnecting the third electrode from an electrical ground, reapplying a constant current to the first circuit at a first time, measuring the maximum voltage difference between the reference voltage and the first voltage at a second time, and calculating, by the processor, the oxidizer concentration of the test fluid based on difference between the first time and the second time. In various embodiments, the method further comprises, calculating, by the processor, the microbe concentration of the test fluid based on difference between the first time and the second time.

In various embodiments, a system comprises a test fluid comprising a concentration of an oxidizing compound, and a measurement device, In various embodiments, the measurement device comprises a processor, a power supply that is configured to provide a constant current, and a first electrode, a second electrode, and a third electrode. In various embodiments, the first electrode and the second electrode are assembled on a circuit to which the constant current is applied when the first electrode and the second electrode are submerged in the test fluid, and the third electrode is not assembled on the circuit, the first electrode, the second electrode, and the third electrode are each comprised of a noble metal, a passivated transition metal, a glass-like carbon, or some combination thereof, the first electrode is configured to measure a reference voltage indicating an electrochemical potential at which electrolysis occurs in the test fluid, the third electrode is configured to measure a first voltage indicating an oxidizing potential of the test fluid, and the measurement device is configured to calculate an oxidizer concentration measurement indicating the concentration of the oxidizing compound in the test fluid based on a voltage difference between the reference voltage and the first voltage.

In various embodiments, a system comprises a test fluid, and a measurement device configured to apply a constant current to the test fluid, measure a reference voltage indicating an electrochemical potential at which electrolysis occurs in the test fluid, measure a first voltage indicating a potential of the test fluid related to one of an oxidizing potential, a pH potential, or an ion concentration chemical potential, and calculate a concentration measurement in the test fluid based on a voltage difference between the reference voltage and the first voltage.

These and other aspects of the present disclosure will become apparent upon reference to the following detailed description and attached drawings. All references disclosed herein are hereby incorporated by reference in their entirety as if each was incorporated individually.

BRIEF DESCRIPTION OF THE DRAWINGS

The subject matter of the present disclosure is particularly pointed out and distinctly claimed in the concluding portion of the specification. A more complete understanding of the present disclosure, however, may be obtained by referring to the detailed description and claims when considered in connection with the following drawings, which illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers. Views in the figures are drawn to scale (unless otherwise noted), meaning the sizes of the depicted elements are accurate relative to each other for at least the embodiment in the view.

Figure 1:
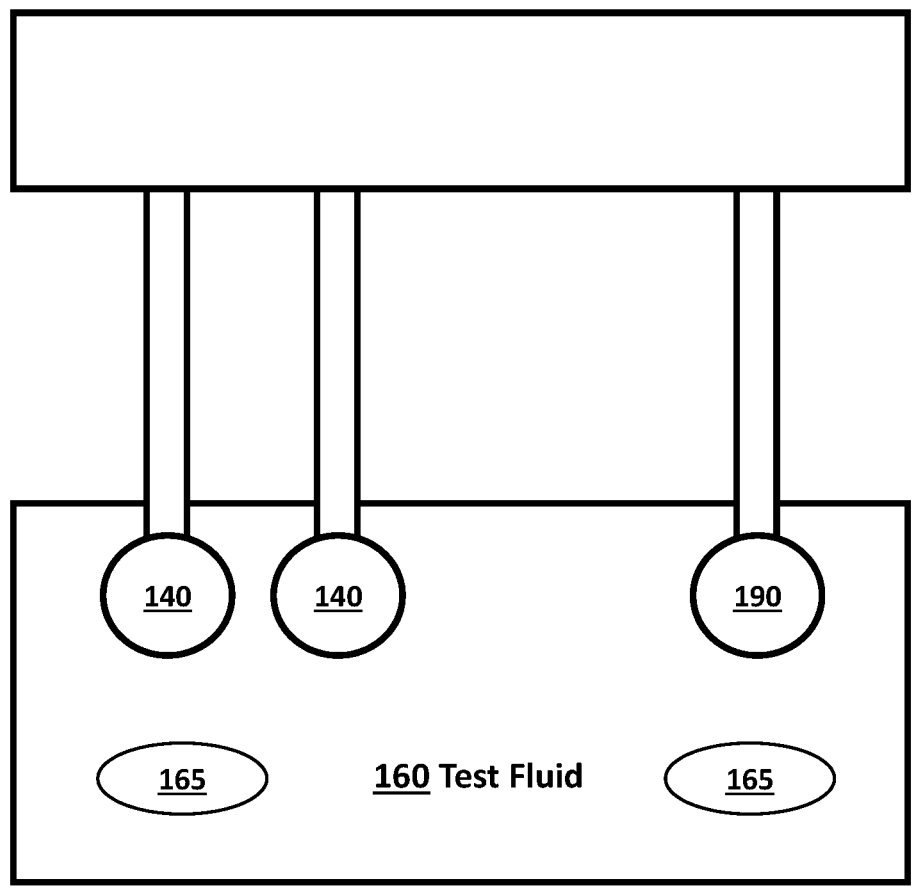
FIG. 1 illustrates a block diagram of an embodiment of a measurement device in accordance with certain embodiments.

For simplicity and clarity of illustration, the drawing figures illustrate the general manner of construction, and descriptions and details of well-known features and techniques may be omitted to avoid unnecessarily obscuring the disclosure. Additionally, elements in the drawing figures are not necessarily drawn to scale. For example, the dimensions of some of the elements in the figures may be exaggerated relative to other elements to help improve understanding of embodiments of the present disclosure. The same reference numerals in different figures denote the same elements.

DETAILED DESCRIPTION

The detailed description of various embodiments herein makes reference to the accompanying drawings, which show various embodiments by way of illustration. While these various embodiments are described in sufficient detail to enable those skilled in the art to practice the disclosure, it should be understood that other embodiments may be realized and that logical, chemical, and mechanical changes may be made without departing from the spirit and scope of the disclosure.

Thus, the detailed description herein is presented for purposes of illustration only and not of limitation. For example, the steps recited in any of the method or process descriptions may be executed in any order and are not necessarily limited to the order presented. Furthermore, any reference to singular includes plural embodiments, and any reference to more than one component or step may include a singular embodiment or step. Also, any reference to attached, fixed, connected, or the like may include permanent, removable, temporary, partial, full, and/or any other possible attachment option. Surface shading lines may be used throughout the figures to denote different parts but not necessarily to denote the same or different materials.

The terms "first," "second," "third," "fourth," and the like in the description and in the claims, if any, are used for distinguishing between similar elements and not necessarily for describing a particular sequential or chronological order. It is to be understood that the terms so used are interchangeable under appropriate circumstances such that the embodiments described herein are, for example, capable of operation in sequences other than those illustrated or otherwise described herein. Furthermore, the terms "include," and "have," and any variations thereof, are intended to cover a non-exclusive inclusion, such that a process, method, system, article, device, or apparatus that comprises a list of elements is not necessarily limited to those elements, but may include other elements not expressly listed or inherent to such process, method, system, article, device, or apparatus.

The terms "left," "right," "front," "back," "top," "bottom," "over," "under," and the like in the description and in the claims, if any, are used for descriptive purposes and not necessarily for describing permanent relative positions. It is to be understood that the terms so used are interchangeable under appropriate circumstances such that the embodiments of the invention described herein are, for example, capable of operation in other orientations than those illustrated or otherwise described herein.

The terms "couple," "coupled," "couples," "coupling," and the like should be broadly understood and refer to connecting two or more elements or signals, electrically, mechanically and/or otherwise. Two or more electrical elements may be electrically coupled together, but not be mechanically or otherwise coupled together; two or more mechanical elements may be mechanically coupled together, but not be electrically or otherwise coupled together; two or more electrical elements may be mechanically coupled together, but not be electrically or otherwise coupled together. Coupling may be for any length of time (e.g., permanent or semi-permanent or only for an instant).

"Electrical coupling" and the like should be broadly understood and include coupling involving any electrical signal, whether a power signal, a data signal, and/or other types or combinations of electrical signals. "Mechanical coupling" and the like should be broadly understood and include mechanical coupling of all types.

The absence of the word "removably," "removable," and the like near the word "coupled," and the like does not mean that the coupling, etc. in question is or is not removable.

As defined herein, the terms "approximately" or "about" can, in some embodiments, mean within plus or minus ten percent of the stated value. In other embodiments, "approximately" or "about" can mean within plus or minus five percent of the stated value. In further embodiments, "approximately" or "about" can mean within plus or minus three percent of the stated value. In yet other embodiments, "approximately" or "about" can mean within plus or minus one percent of the stated value.

The embodiments described herein provide a variety of advantages over conventional measurement devices and probes. These advantages may include the ability to extend the lifetime of the measurement device and/or to increase the reliability of any measurements taken using the measurement device. This can be attributed, at least in part, to one or more of the electrolysis-based techniques utilized to take measurements, and/or to the structure of the disclosed embodiments. The structure of the disclosed embodiments may utilize noble metals, passivated transition metals, and/or glassy carbons for electrodes immersed in the test fluid. The structure of the disclosed embodiments may omit a junction, which is susceptible to clogging, poisoning, and mechanical failure in conventional devices. Advantages may include the ability of the disclosed embodiments to operate in a reverse polarization mode that allows a measurement device to self-clean the surfaces of electrodes. Advantages of the disclosed embodiments may include the ability to operate in a chronopotentiometric mode to take measurements that can be used to confirm the measurements taken during normal operation. This technology-based solution marks an improvement over existing measurement devices and probes.

Potentiometric Mode

Referring now to the drawings, and more particularly to FIG. 1, shown therein and designated by the reference numeral 100 is a first embodiment of the present measurement device 150. In the embodiment shown, measurement device 150 is configured to detect and/or measure oxidizing compounds in test fluids in a potentiometric mode. In various embodiments, measurement device 150 uses electrolysis to measure oxidizing compounds (e.g. ozone) in test fluids, such as drinking water and/or other types of water using oxidation reduction potential (ORP) measurement techniques.

In various embodiments, measurement device 150 comprises at least three electrodes. Measurement device 150 may comprise two reference electrodes 140 and one sensor electrode 190. The two reference electrodes 140 may be configured on a circuit as a reference pair. The circuit may comprise a first circuit of measurement device 150. In various embodiments, sensor electrode 190 may be excluded from the circuit with reference electrodes 140. In various embodiments, when reference electrodes 140 and sensor electrode 190 of measurement device 150 are submerged in a test fluid 160, and a constant current is applied to the pair of reference electrodes 140, electrolysis splits the molecules of test fluid 160, and the electrochemical potential at which electrolysis occurs is used as a reference voltage. For example, when test fluid 160 is water, the pair of reference electrodes 140 electrolyzes the water to split the molecules into hydrogen and oxygen. Reference electrodes 140 may conduct water oxidation and/or water reduction and, therefore, evolve oxygen gas or hydrogen gas. In various embodiments, the constant current applied is about 10 microamperes (uA) (wherein about means+/−2 uA). However, any suitable current may be applied to the reference electrodes.

In various embodiments, sensor electrode 190 is coupled to one reference electrode 140 of the reference electrode pair using a high impedance resistor, an operational amplifier, and/or another component. By measuring the voltage across this connection, a first voltage difference between reference electrodes 140 and sensor electrode 190 may be calculated. As oxidizing compounds 165 are added to test fluid 160 (e.g., to sanitize test fluid 160), the potential on the sensor electrode may increase, and the measured voltage across the connection between the pair of reference electrodes 140 and the sensor electrode 190 may change. In various embodiments, a second voltage difference between reference electrodes 140 and sensor electrode 190 is calculated. The first voltage difference may be compared to the second voltage difference. Because the voltage difference between reference electrodes 140 and sensor electrode 190 is relative to the concentration of oxidizing compounds 165, the comparison of the first voltage difference and the second voltage difference may be calibrated as, or otherwise used to calculate, an oxidizer concentration measurement (e.g., $V_{ac}$ in FIG. 3). The oxidizer concentration measurement may indicate the amount of oxidizing compounds 165 in the test fluid 160.

In various embodiments, one of reference electrodes 140 included in the reference electrode pair measures a voltage indicating an electrochemical potential at which electrolysis occurs in test fluid 160. In various embodiments, sensor electrode 190 measures a voltage indicating an oxidizing potential of test fluid 160. Measurement device 150 may then subtract the voltage measured by sensor electrode 190 from the voltage measured by reference electrode 140 to calculate the oxidizer concentration measurement.

Figure 3:
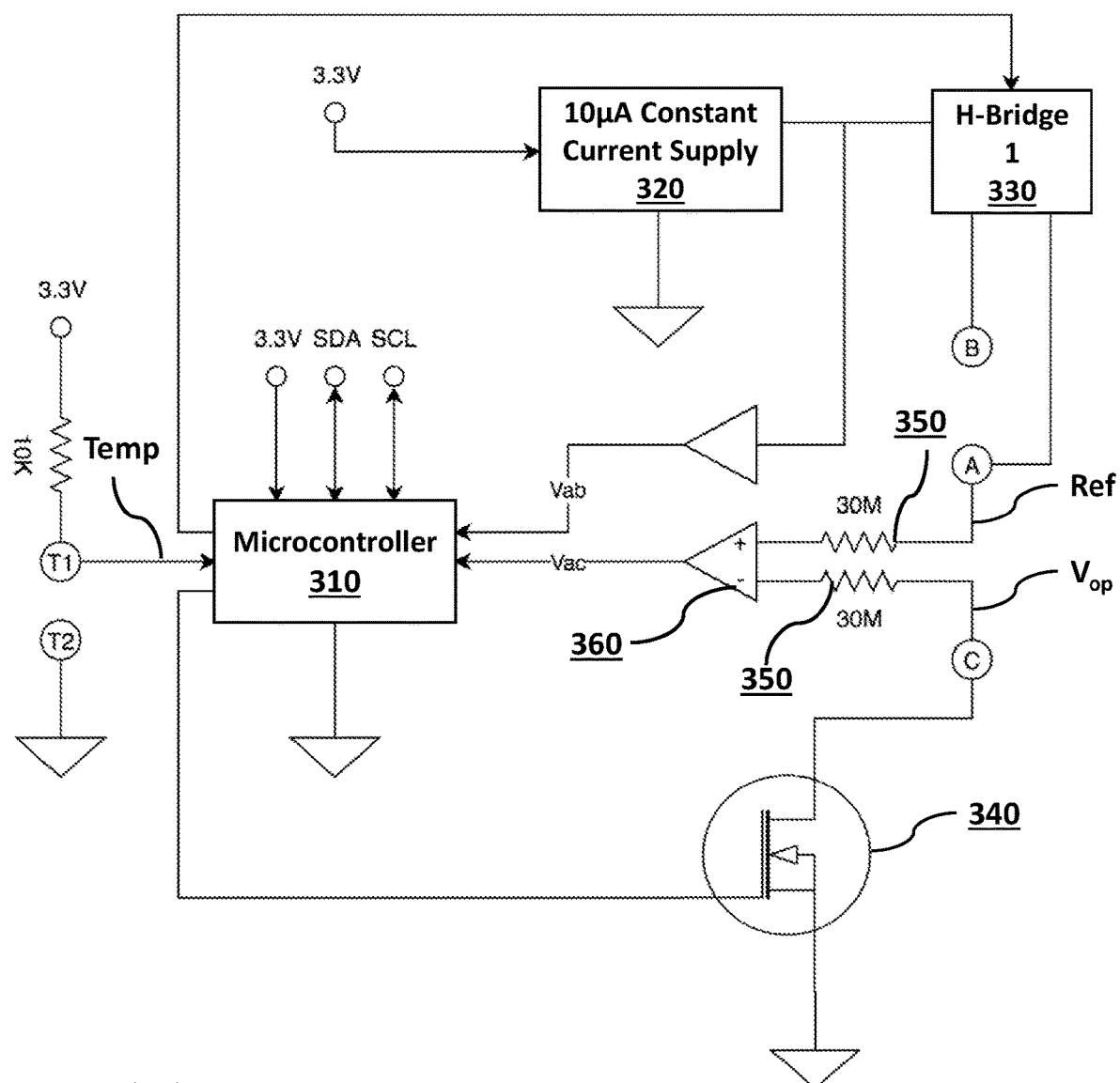
FIG. 3 illustrates a circuit diagram of a control board that may be utilized by a measurement device in accordance with certain embodiments.

In various embodiments, the concentration of oxidizer may be calculated using the following equation:

$$\text{Oxidizer Concentration} = \text{EXP}\left(\frac{[\Delta 6 \text{ SO}_3] - C_0}{C_1}\right)$$

wherein $\Delta 6S\ O_3$ is the difference between (1) the voltage measured between sensor electrode 190 and a reference electrode 140 (i.e., $V_{ac}$ as seen in FIG. 3) and (2) the voltage between reference electrodes 140 (i.e., $V_{ab}$ as seen in FIG. 3), and wherein $C_0$ and $C_1$ are coefficients.

In various embodiments, measurement device 150 is used to detect and/or measure oxidizing compounds 165 in various test fluids 160. In certain embodiments, test fluid 160 comprises water (e.g., drinking water, non-potable water, distilled water, deionized water, and/or other types of water). In various embodiments, test fluid 160 comprises one or more alcohols (e.g., ethanol, methanol, and other alcohols) and/or electrolyze-able organic solvents (e.g., acetic acid).

In various embodiments, measurement device 150 is used to detect and measure various types of oxidizing compounds 165. Such oxidizing compounds 165 include, but are not limited to, any one or more of the following: oxygen ($O_2$), ozone ($O_3$), hydrogen peroxide ($H_2O_2$) (as well as other inorganic peroxides), fluorine ($F_2$), chlorine ($Cl_2$), halogen compounds, nitric acid ($HNO_3$), nitrate compounds, sulfuric acid ($H_2SO_4$), peroxydisulfuric acid ($H_2S_2O_8$), peroxymonosulfuric acid ($H_2SO_5$), chlorite, chlorate, perchlorate, hypochlorite (and other hypohalite compounds), household bleach (NaClO), hexavalent chromium compounds (e.g., chromic and dichromic acids and chromium trioxide, pyridinium chlorochromate, and chromate/dichromate compounds), permanganate compounds (e.g., potassium permanganate), sodium perborate, nitrous oxide ($N_2O$), nitrogen dioxide ($NO_2$), dinitrogen tetroxide ($N_2O_4$), potassium nitrate ($KNO_3$), and/or sodium bismuthate.

In various embodiments, measurement device 150 is used to detect and measure various types of reducing compounds. Such reducing compounds include, but are not limited to, any one or more of the following: hydrogen, diborane, sodium borohydride ($NaBH_4$), sulfur dioxide, sulfite compounds, dithionates (e.g., $Na_2S_2O_6$), thiosulfates (e.g., $Na_2S_2O_3$), iodides (e.g., KI), hydrazine, diisobutylaluminium hydride (DIBAL-H), oxalic acid, formic acid (HCOOH), ascorbic acid ($C_6H_8O_6$), reducing sugars, phosphites, hypophosphites, phosphorous acid, dithiothreitol (DTT), carbon monoxide (CO), cyanides, carbon (C), tris-2-carboxyethylphosphine hydrochloride (TCEP), compounds containing the Fe2+ ion (e.g., such as iron(II) sulfate), and/or compounds containing the Sn2+ ion (e.g., such as tin(II) chloride).

Self-Cleaning Mode

In various embodiments, measurement device 150 is configured to execute a self-cleaning function on one or more of electrodes 140 and 190. During normal operation (e.g., when measurement device 150 is operating in a potentiometric mode and is being utilized to measure and/or control levels of oxidizing compounds 165 in test fluid 160), the surface of electrodes 140 and 190 may be reduced, thereby causing a gain in electrons. For example, in embodiments where the test fluid comprises water, operation of measurement device 150 causes one of the reference electrodes 140 to reduce water resulting in the evolution of hydrogen gas. Under such circumstances, this reference electrode may have the ability to reduce other constituents in the test fluid, for example, by reducing metals present in the test fluid onto the surface of this reducing reference electrode. Stated differently, the reference electrode 140 comprising a reducing electrode may undergo fouling in certain environments.

To combat fouling of the reducing electrode, measurement device 150 can be operated in a reverse polarization mode that executes the self-cleaning function. During use in the reverse polarization mode, measurement device 150 utilizes an H-bridge, or other equivalent electrical component, to reverse the current that is applied to the pair of reference electrodes 140. This reversal of the current can produce a redox (or reduction-oxidation) reaction on the reference electrodes 140, which is inverse to that current used during normal operation and which reverses the reduction by oxidizing the surface of electrodes 140 and 190. Stated differently, in potentiometric mode, a first reference electrode may function as a reducing electrode and a second reference electrode may function as an oxidizing electrode; in reverse polarization mode, the first reference electrode may function as an oxidizing electrode and the second reference electrode may function as a reducing electrode.

Operation of reverse polarization mode may correct and/or reverse electrode fouling that occurred during prior operation of potentiometric mode. Operation of reverse polarization mode may preserve and/or extend the functional life of one or more electrode 140, 190 of measurement device 150. Operation of reverse polarization mode may improve the efficacy and/or accuracy of measurements taken by one or more electrode 140, 190 and/or calculations made by measurement device 150.

Chronopotentiometric Mode

In various embodiments, measurement device 150 takes measurements of oxidizing compounds 165 when operating in chronopotentiometric mode. Chronopotentiometric mode may be configured for measurement of oxidizer concentrations above a certain threshold. In various embodiments, oxidizer concentrations are sufficiently high that the sensor electrode may become saturated with oxidized compounds. Under such circumstances, the ability of measurement device 150 to calculate oxidizer concentration may be affected. In various embodiments, the measurements taken by measurement device 150 in chronopotentiometric mode can be used to confirm the accuracy of the measurements taken by measurement device 150 in the potentiometric mode.

In various embodiments, to calculate oxidizer concentration in chronopotentiometric mode, measurement device 150 shorts one or more of electrodes 140 and 190 to an electrical ground, which has the effect of applying a reducing potential between electrodes 140 and 190, and purging the surface of electrodes 140 and 190 of oxidizing compounds 165 by a process of electrochemical reduction. Thereafter, the communication of an electrical current to sensor electrode 190 may be ceased such that current is applied to the reference electrodes 140 but not to the sensor electrode 190.

Sensor electrode 190, after being shorted and/or purged of all or substantially all the oxidizing compounds on its surface, may begin again to be oxidized by oxidizing compounds present in the test fluid. The concentration of oxidizing compounds 165 may be calculated by measuring both the maximum voltage at sensor electrode 190 (i.e., the voltage at which the sensing electrode is again saturated with oxidizing compounds) and the time to reach that maximum voltage. In various embodiments, the recovery time will be shorter and/or the maximum voltage will be higher for test fluids comprising higher concentrations of oxidizing compounds 165, and the recovery time will be longer and/or the maximum voltage will be lower for test fluids comprising lower concentrations of oxidizing compounds.

As described above, the difference between the maximum voltage and the reference electrode voltage (i.e., the maximum voltage difference) may be used to calculate an oxidizer concentration of the test fluid. In various embodiments, the recovery time (i.e., the time for the sensor electrode to reach maximum voltage after being shorted and again beginning to be oxidized) may be used to calculate an oxidizer concentration of the test fluid. Accordingly, a chronopotentiometric measurement of oxidizer concentration can be determined by measurement device 150.

Figure 9:
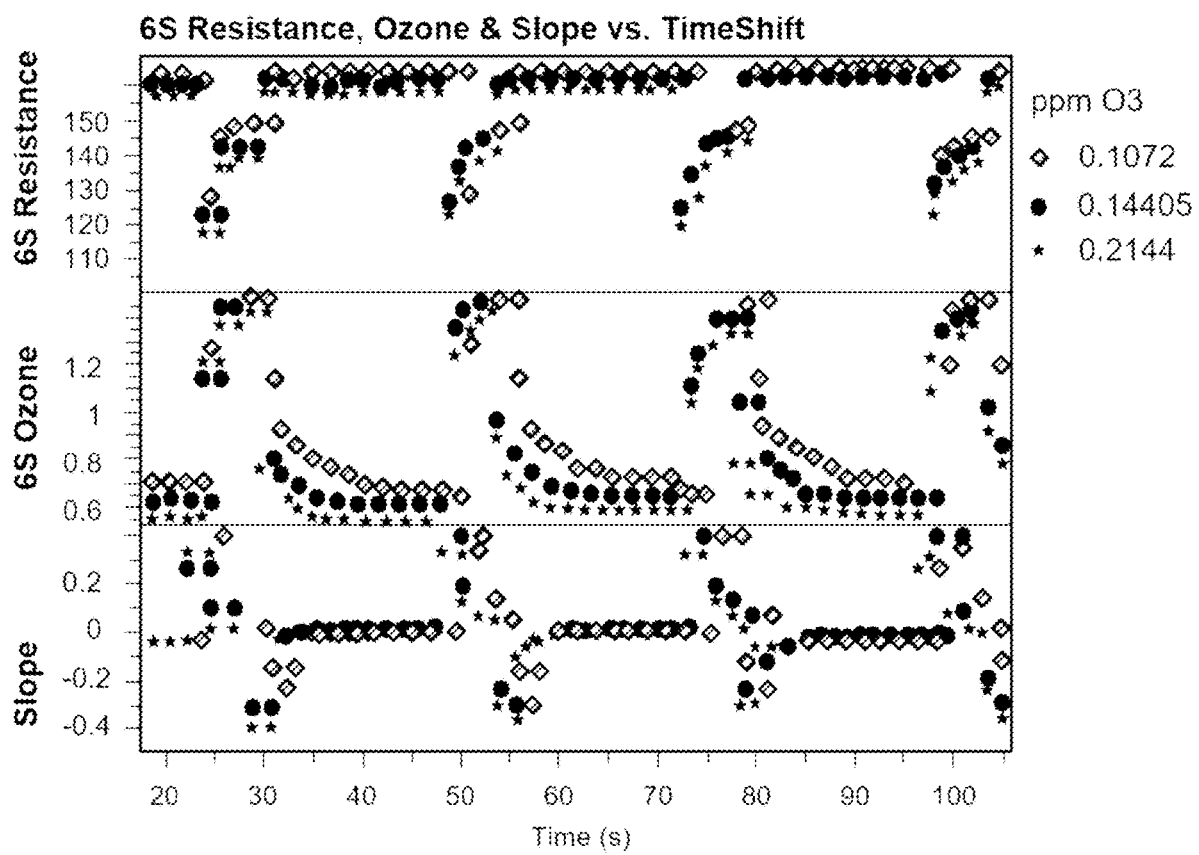
FIG. 9 illustrates data showing the ozone concentration and sensor electrode resistance during chronopotentiometric mode in accordance with certain embodiments.

FIG. 9 illustrates the measurement of ozone concentration over time by a sensor electrode 190 of a measurement device 150 as described herein, after the sensor electrode 190 is shorted to the electrode performing reduction (the cathode of the reference cell) and "purged" of oxidizing compounds. As shown in FIG. 9, at higher concentrations of ozone, the surface of the sensor electrode 190 is more quickly oxidized on the sensor electrode than at lower concentrations of ozone, as seen in the measured presence over time of "6S ozone." Moreover, FIG. 9 illustrates that the 6S resistance measurement may be unaffected by changes in ozone concentration, confirming that hydrolysis by the reference electrode pair 140 may be used as a reference reaction for the sensor electrode 190. The slope measurement illustrated in FIG. 9 may further provide an input for the control programming and may serve as a summary of the chronopotentiometric data.

Dual Cleaning and Measuring

Figure 2:
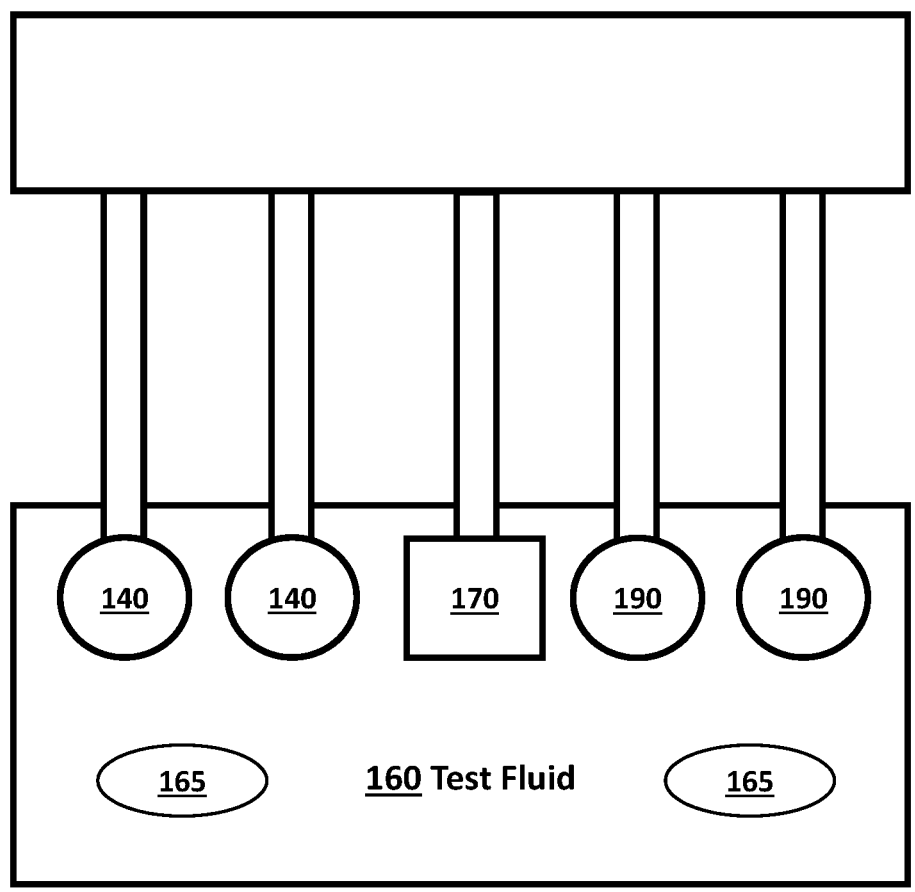
FIG. 2 illustrates a block diagram of another embodiment of a measurement device in accordance with certain embodiments.

In various embodiments, as illustrated in FIG. 2 and designated by the reference numeral 200, a second embodiment of measurement device 150 includes a fourth electrode 190, which is paired with sensor electrode 190, thus allowing either pair of electrodes to be used as a reference pair in taking measurements and/or to implement the self-cleaning procedure. Stated differently, the fourth electrode 190 and the sensor electrode 190 may be configured on a circuit together and may operate, optionally, as a second electrode pair as reference electrodes when one reference electrode 140 is operates, optionally as a sensor electrode. This circuit may comprise a second circuit of measurement device 150.

In order to facilitate simultaneous sensing and self-cleaning functions of measurement device 150, during a first cycle, a reference pair of electrodes 140 and one electrode of a sensor electrode pair 190 are used as described herein to determine oxidizer concentrations in a test fluid. During the first cycle, one of the reference pair of electrodes 140 may operate as a cathode and one of the reference pair of electrodes 140 may operate as an anode. During a second cycle, the electrode 140 previously operating as an anode may now operate as a sensor electrode and the pair of sensor electrodes 190 may now operate as a reference pair of electrodes. Reversing polarization in this way may cause cleaning of any electrode fouled during operation of measurement device 150.

In various embodiments, four electrodes of measurement device 150 can be used interchangeably as reference electrodes or as sensor electrodes. In order to facilitate simultaneous sensing and self-cleaning functions of measurement device 150, four electrodes of measurement device 150 may be arrange in a round-robin fashion such that their functions as reference electrodes or as sensor electrodes changes in progressive cycles of measurement device 150.

In such embodiments, during a first cycle, a first electrode may function as the anode of a reference pair as previously described; a second electrode may function as the cathode of a reference pair as previously described, potentially becoming fouled over time; and a third electrode may function as the sensor electrode as previously described. During a second cycle, the second electrode may function as the anode of the reference pair, causing reduced compounds on its surface to oxidize and, thereby reversing any electrode fouling; the third electrode may function as the cathode of the reference pair, potentially becoming fouled over time;

and a fourth electrode may function as the sensor electrode as previously described. During a third cycle, the third electrode may function as the anode of the reference pair, causing reduced compounds on its surface to oxidize and, thereby reversing any electrode fouling; the fourth electrode may function as the cathode of the reference pair, potentially becoming fouled over time; and the first electrode may function as the sensor electrode as previously described. During a fourth cycle, the fourth electrode may function as the anode of the reference pair, causing reduced compounds on its surface to oxidize and, thereby reversing any electrode fouling; the first electrode may function as the cathode of the reference pair, potentially becoming fouled over time; and the second electrode may function as the sensor electrode as previously described.

Microbial Sensing

In various embodiments, measurement device 150 is used to detect and measure microbial life in test fluid 160. For example, because aerobic microbial life consumes oxygen in order to live and propagate, microbes present in test fluid 160 may reduce the oxidizing compounds 165 present in test fluid 160 over time. This reduction of oxidizing compounds 165 in test fluid 160 can therefore be used to measure the microbial life concentration and/or content as a function of the oxidizer concentration measurement.

Figure 10:
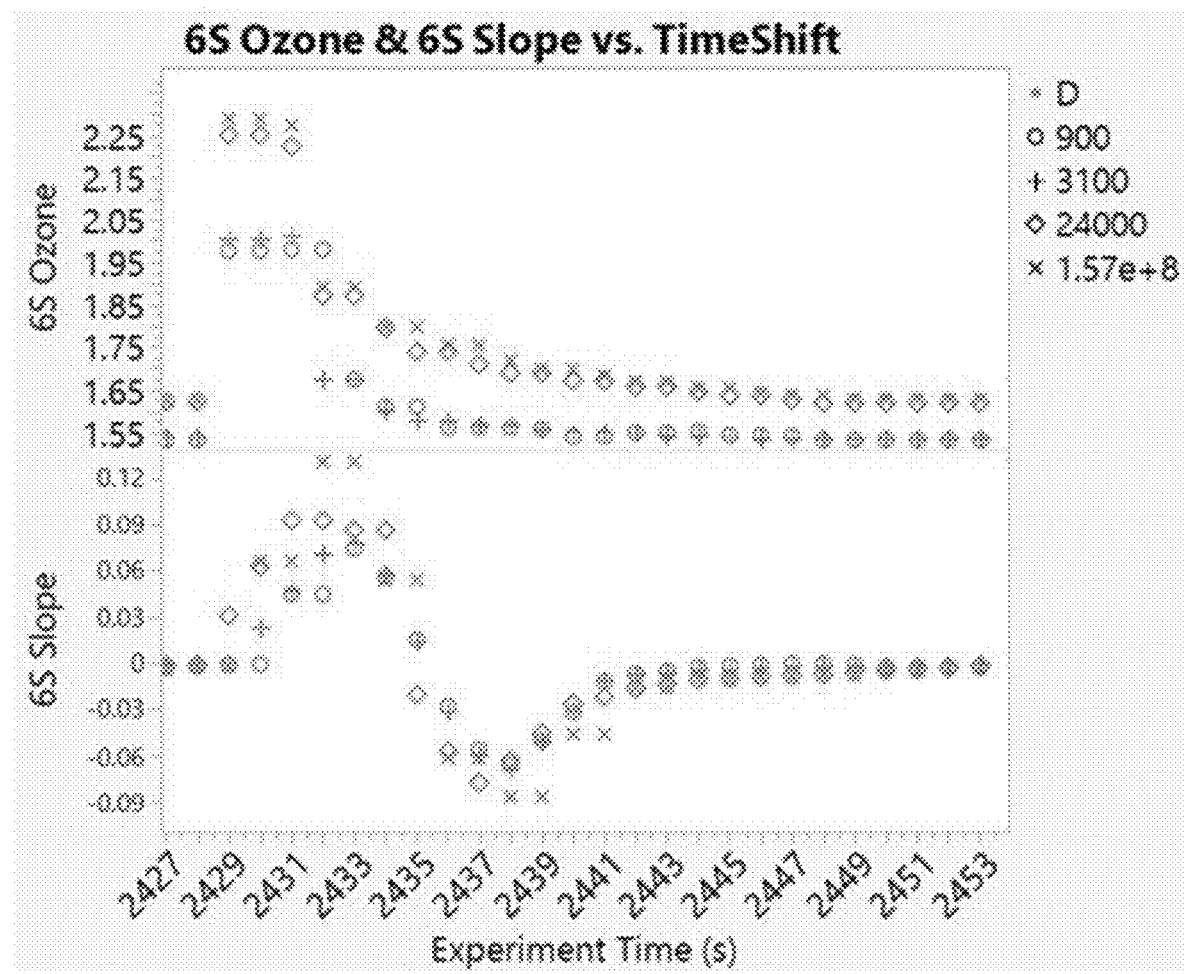
FIG. 10 illustrates data showing the sensor electrode resistance of test samples having various microbe concentrations in accordance with certain embodiments.

As illustrated in FIG. 10, the concentration of colony forming units ("CFUs") of microbes can be detected by measurement device 150. As aqueous solution was tested by heterotrophic plate count for the presence of microbes. When the presence of microbes was confirmed, the water was diluted by various amounts with deionized water to produce several samples having a variety of known microbe concentrations.

Potassium Carbonate was added to each sample to a conductivity of 75 microSiemens+/−5 microSiemens. Each sample was tested by a measurement device, as described herein, in chronopotentiometric mode. Each test lasted for at least 2 hours. This allowed for at least 288 chronopotentiometric purge pulse events at 25 s each. The data was recorded at a data collection rate of 1 data point per second.

FIG. 10 shows a single chronopotentiometric purge pulse event on one sensor at various microbe content levels (about $1.57 \times 10^8$ CFU ("x"), about 24,000 CFU ("◇"), about 3,100 CFU ("+"), about 900 CFU ("o"), and control ("•")). The purge pulse begins at experiment time 2430$s$ and ends 5 seconds later. The following 25 seconds shows the recovery of the voltage signal from the purge state. At the end of 20$s$ a subsequent purge pulse event occurs. FIG. 10 illustrates that test fluids having high microbe concentrations (above 50,000 CFU) produce a maximum 6S O3 (ozone) voltage value above about 2.2V, while water with smaller microbe concentrations produce 6S ozone values below about 2.2V under the same experimental conditions. The 6S Slope curve of FIG. 10 further illustrates the first derivative of the 6S ozone curve above, i.e., the slope of that curve. The 6S Slope curve may confirm the difference between test fluids having low and high microbe concentrations water, such that the slope may be used as a control signal for future measurements in addition to the raw 6S ozone voltage value.

In various embodiments, microcontroller 310 (hereinafter described) uses microbe concentration measurements to implement the control function for increasing and/or decreasing the concentration of ozone in the water. In various embodiments, microcontroller 310 compares the measured microbe concentration to a library of pre-stored conditions to activate and/or deactivate an oxidizer generator (hereinafter described). Measurement device 150 may use microcontroller 310 to control the current that is applied to the test fluid and/or to control the oxidizing compounds that are applied to the test fluid in response to a CFU count that is higher than a predetermined threshold. In various embodiments, the predetermined threshold for CFU count is 24,000 CFU/100 mL. In various embodiments, measurement device 150 may activate an oxidizer generator in response to a measured voltage at sensor electrode 190 at and/or above about 2.2V.

Additional Features

In various embodiments, each of electrodes 140 and 190 are constructed of a noble metal, a passivated transition metal, or a glass-like carbon (also referred to as "glassy carbons" or "vitreous carbons"). In various embodiments, electrodes 140 and 190 are constructed of gold, platinum, titanium, or a glass-like carbon, or of some combination thereof. Electrodes 140 and 190 can additionally, or alternatively, be constructed of other similar metals, compounds, or other materials that do not oxidize under the conditions applied to measurement device 150 when submerged in test fluid 160. Using such construction materials avoids the risk of corrosion, which can have undesired effects such as reducing the lifetime of measurement device 150, eluting ions into test fluid 160, and causing measurement device 150 to become insensitive to oxidizing compounds 165 being measured.

In various embodiments, as illustrated in FIG. 2, measurement device 150 comprises a temperature measurement component 170 that is configured to measure or determine the temperature of test fluid 160. In various embodiments, temperature measurement component 170 comprises a thermistor and/or other device that is capable of measuring the temperature of test fluid 160. Ozone is unstable and very reactive, capable of reacting with itself such that ozone will revert to oxygen. This reaction is temperature sensitive. The reaction rate increases with increasing temperature. Therefore, a measurement of temperature is a prediction of ozone half-life. The temperature readings are generated by a thermistor as a drop across a resistor that is a function of temperature. The temperature readings generated by temperature measurement component 170 may be used by measurement device 150, along with other data (e.g., oxidizer concentration measurements) to adjust and/or control (e.g., to increase or decrease) the concentration of oxidizing compounds 165 in test fluid 160.

Measurement device 150 may comprise additional sensors including, for example, one or more pH sensors, proton selective electrodes, ion selective electrodes, or the like. In various embodiments, the electrodes 140 and 190 in measurement device 150 comprise one or more pH electrodes and/or proton selective electrodes configured to take pH measurements, acid concentration measurements, base measurements, and/or other similar measurements. These electrodes may be useful for measuring pH, acid concentration, base concentration, etc. in test fluids other than water. In various embodiments, electrodes 140 and 190 include one or more ion selective electrodes (ISE) configured to apply electrolysis to test fluid 160 for taking ion concentration measurements.

FIG. 3 illustrates a circuit diagram of a control board 300 that may be utilized by a measurement device (e.g., measurement device 150 in FIGS. 1 and 2) in accordance with certain embodiments. In various embodiments, control board 300 is utilized for a measurement device that is assessing water and applying ozone as an oxidizing compound to sterilize the water.

In various embodiments, control board 300 comprises: a microcontroller 310, a power supply 320, an H-bridge 330, a MOSFET (metal-oxide-semiconductor field-effect transistor) 340, a pair of resistors 350, and an operational amplifier (op amp) 360. In an exemplary embodiment, power supply 320 provides about 10 microamperes (uA) (wherein about means+/−2 uA) as a constant current supply, the MOSFET 340 is an N-channel MOSFET, the op amp 360 is a differential op amp, and resistors 350 are input resistors providing about 30 megaohms (Mohms) (wherein about means+/−5 Mohms) in resistance. In other embodiments, different types of components may be integrated into control board 300 based on the test fluid and/or based on the types of measurements that are being deduced.

In various embodiments, control board 300 includes three electrical connections—A, B, and C—for each of three connected electrodes (e.g., electrodes 140 and 190 in FIG. 1). For example, in certain embodiments, the three electrical connections-A, B, and C—are connected to wires, and the electrodes are attached to the end of the wires and suspended in the test fluid. In FIG. 3, the electrical connections A and B correspond to the pair of reference electrodes, and the electrical connection C corresponds to the sensor electrode. As explained above, in other embodiments, such as depicted in FIG. 2, the measurement device includes a fourth electrode. In such embodiments, an additional electrical connection is added to control board 300 to facilitate connection of the fourth electrode. The fourth node can be included on a circuit with the electrical connection C corresponding to the sensor electrode. T1 and T2 are electrical connections to a temperature measurement component (e.g., temperature measurement component 170 in FIGS. 1 and 2).

Power supply 320 may be configured to regulate a fixed current by adjusting the output voltage as the load changes. In various embodiments, constant current power supply provides a regulated about 1 to about 10 μA of current based on a change in output voltage ranging from approximately 0 to 3 VDC (volts DC). The constant current supply may be implemented using an instrumentation operational amplifier. When the current is applied to electrical connections A and B, the water or test fluid is electrolyzed, and this circuit is used to produce $V_{ab}$, which is a measure of the test fluid conductivity, and Ref, which is a measure of the electrochemical potential at which electrolysis occurs in the test fluid. Under ideal conditions, water electrolysis occurs at ~1.23 V (volts). However, Ref reflects the true voltage for performing electrolysis and, thus, can vary based on actual operating conditions (e.g., based on the separation distance of the electrodes). Electrode 190, connected through connection C measures a voltage indicating an oxidizing potential of the test fluid, which is shown as $V_{op}$. Ref and $V_{op}$ are passed through resistors 350 and supplied to op amp 360. Op amp 360 subtracts $V_{op}$ from Ref to produce $V_{ac}$, which serves as an indicator of the oxidation potential voltage. T1 is the electrical connection to the temperature measurement component and T2 is a connection to a ground associated with the temperature measurement component. Temp is a voltage indicating the temperature of the test fluid.

Microcontroller 310 receives the following inputs:
(1) $V_{ab}$: this is the test fluid electrolysis cell voltage (Vab=A−B) and serves as an indicator of test fluid conductivity;
(2) $V_{ac}$: this is the oxidizer concentration measurement (for example, an ozone concentration measurement) and serves as an indicator of the oxidation potential voltage ($V_{ac}$=A−C);
(3) Temp: this is a temperature measurement of the test fluid received from the temperature measurement component (e.g., thermistor);
(4) 3.3 V: this is the power supplied to control board 300; and
(5) SDA/SCL: these are $I^2C$ network signals between microcontroller 310 and a host controller.

The outputs of microcontroller 310 include:
(1) H-Bridge 330 output signal: this output controls the current flow and instructs the H-Bridge 330 whether the current should be reversed (e.g., depending upon whether not the device is operating in the normal mode or the reverse polarization mode);
(2) MOSFET 340 output signal: this output controls whether or not electrode C is connected to a ground by sending instructions to the MOSFET 340; and
(3) SDA/SCL output signals: these outputs are provided as part of an $I^2C$ network and can communicate the electrode voltage measurements ($V_{ab}$ and $V_{ac}$) as well as the temperature measurement (T1) upon request from the host controller.

In various embodiments, microcontroller 310 uses the electrode voltage measurements ($V_{ab}$ and $V_{ac}$) as well as the temperature measurement (T1) to implement the control function for increasing and/or decreasing the concentration of ozone in the water. In various embodiments, microcontroller 310 compares these parameters to a library of pre-stored conditions to activate and/or deactivate an ozone generation system. The library may use the temperature measurement, and other measurements, to control the current that is applied to the test fluid and/or to control the oxidizing compounds that are applied to the test fluid.

As discussed above, measurement device 150 can operate in a potentiometric mode (e.g., during normal operation when the concentration of the ozone or other oxidizing compound is being measured), a chronopotentiometric mode (e.g., during an operation that cleans the sensor electrode and/or takes confirmatory measurements), and a reverse polarization mode (e.g., during a self-cleaning operation that cleans the electrodes and/or takes confirmatory measurements). When operating in the potentiometric mode, the H-Bridge output signal provided by microcontroller 310 can instruct the H-Bridge 330 that the current flow is not to be reversed, and the MOSFET output signal can instruct MOSFET 340 that electrode 190 corresponding to electrical connection C is not to be connected to a ground. When operating in reverse polarization mode, the H-Bridge output signal provided by microcontroller 310 can instruct H-Bridge 330 that the current flow is to be reversed. When operating in chronopotentiometric mode the MOSFET output signal can instruct MOSFET 340 that the electrode corresponding to electrical connection C is to be connected to a ground. Connecting to the ground will close a circuit between electrode C and the ground, and will result in a "purge" that is intended to reduce any residual oxidizer on the surface of the electrode.

In various embodiments, the SDA/SCL connections connect microcontroller 310 to a host controller. In certain embodiments, microcontroller 310 communicates the electrode voltage measurements and temperature measurements upon request from the host controller. In various embodiments, microcontroller 310 also receives commands from the host controller for controlling H-bridge 330 for electrical connections A and B, and MOSFET 340 (e.g., which may be an N-channel MOSFET) for electrical connection C.

Figure 4:
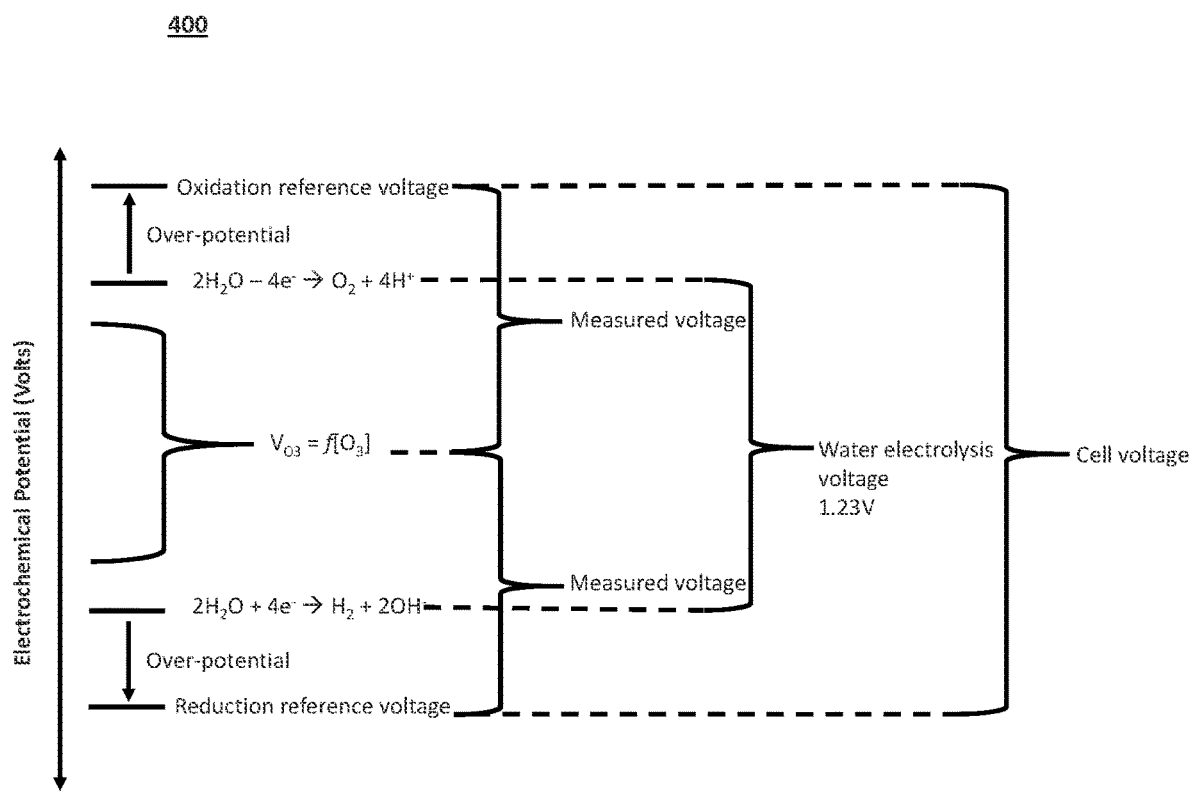
FIG. 4 illustrates a diagram illustrating how measurements are computed in accordance with certain embodiments.

FIG. 4 is a diagram 400 illustrating how measurements are computed in accordance with certain embodiments. This diagram illustrates how measurements may be computed by the measurement device (e.g., measurement device 150 in FIGS. 1 and 2) for various embodiments in which ozone concentration is being measured in water.

The axis on the left represents a range of possible voltages associated with the electrochemical potential at which the process of water electrolysis occurs. This axis is not labeled because the values may be dependent on the type of electrodes that are used. The bracket labeled "Water Electrolysis Voltage 1.23V" represents the voltage to perform water electrolysis under standard conditions. On the far right side, there is a bracket labeled "Cell voltage" that represents the measurement of voltage used to conduct water electrolysis, which considers all features of the true voltage measurement (e.g., such as the area of the test fluid and the distance or separation of the electrodes).

The "Over-potentials" for the reference electrodes represent the difference between the cell voltage and the standard water electrolysis voltage. The electrochemical reactions for water electrolysis also are listed in the figure. An ozone voltage is a function of ozone concentration and can be any value in a range that falls within the water electrolysis reaction voltages. The difference between this voltage and the voltage of the reference is reported as the oxidation potential measurement. In certain embodiments, the reference electrodes are conducting water oxidation and, therefore, are evolving oxygen gas. The reference electrodes can additionally, or alternatively, conduct water reduction and, therefore, evolve hydrogen gas.

Oxidizer Measurement System

Figure 5:
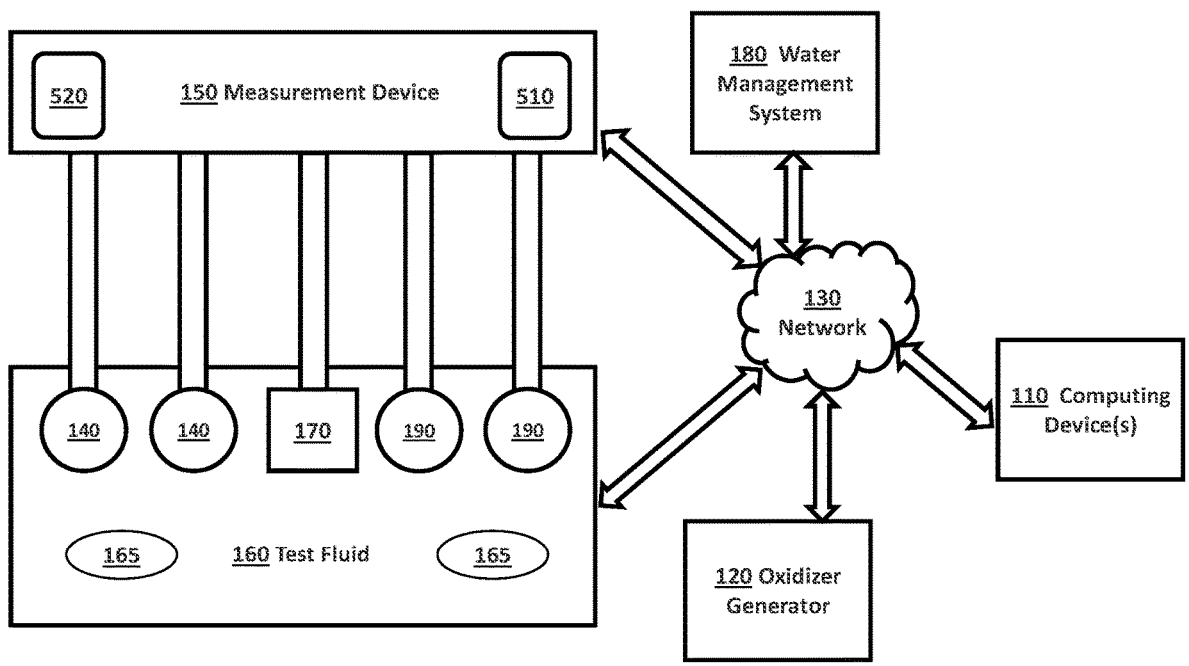
FIG. 5 illustrates block diagram of a system in accordance with certain embodiments.

Referring to FIG. 5, shown therein and designated by the reference numeral 500 is an embodiment of an oxidizer measurement system. Oxidizer measurement system 500 is merely exemplary, and embodiments of the system are not limited to the embodiments presented herein. In various embodiments, oxidizer measurement system 500 comprises: (i) test fluid 160 comprising a concentration of oxidizing compound 165; and (ii) measurement device 150 configured to: apply a constant current to test fluid 160; measure a reference voltage indicating an electrochemical potential at which electrolysis occurs in test fluid 160; measure a second voltage indicating an oxidizing potential of test fluid 160; and calculate an oxidizer concentration measurement indicating the concentration of oxidizing compound 165 in test fluid 160 based on a voltage difference between the reference voltage and the second voltage.

In various embodiments, measurement device 150 of oxidizer measurement system 500 comprises: (a) a processor 510; (b) a power supply 520 that is configured to provide a constant current; and (c) a pair of reference electrodes 140 and at least one sensor electrode 190, wherein reference electrodes 140 are included on a circuit to which the constant current is applied when reference electrodes 140 are submerged in the test fluid, and one or more sensor electrodes 190 are not included on the circuit; reference electrodes 140 and sensor electrodes 190 are each comprised of a noble metal, a passivated transition metal, a glass-like carbon, or some combination thereof, one of the reference electrodes 140 is configured to measure a reference voltage indicating an electrochemical potential at which electrolysis occurs in test fluid 160; sensor electrode 190 is configured to measure a second voltage indicating an oxidizing potential of test fluid 160; and measurement device 150 calculates an oxidizer concentration measurement indicating the concentration of oxidizing compound 165 in test fluid 160 based on a voltage difference between the reference voltage and the second voltage.

In various embodiments, measurement device 150 of oxidizer measurement system 500 a system is configured to: apply a constant current to the test fluid; measure a reference voltage indicating an electrochemical potential at which electrolysis occurs in test fluid 160; measure a second voltage indicating a potential of test fluid 160 related to one of an oxidizing potential, a pH potential, or an ion concentration chemical potential; and calculate a concentration measurement in test fluid based 160 on a voltage difference between the reference voltage and the second voltage.

In various embodiments, measurement device 150 of oxidizer measurement system 500 includes temperature measurement component 170 immersed in test fluid 160. Test fluid 160 may be a liquid or a gas. In various embodiments, oxidizer measurement system 500 further comprises a computing device(s) 110, a water management system 180, and an oxidizer generator 120. In various embodiments, one or more of computing device(s) 110, measurement device 150, water management system 180, and oxidizer generator 120 are in indirect communication with each other over a network 130. In various embodiments, one or more of computing device(s) 110, measurement device 150, water management system 180, and oxidizer generator 120 are in direct communication with each other. Network 130 may represent any type of communication network, e.g., one that comprises a local area network (e.g., a Wi-Fi network), a personal area network (e.g., a Bluetooth network), a wide area network, an intranet, the internet, a cellular network, and/or other types of networks. Although FIG. 5 depicts a single one of each of computing device 110, measurement device 150, water management system 180, and oxidizer generator 120, it should be understood this is not intended to be limiting, and the system can include any number of each component (e.g., computing devices 110, measurement devices 150, water management systems 180, and oxidizer generators 120) and sub-components (e.g., electrodes 140 and 190, and temperature measurement components 170), and all of the components and sub-components can be configured to communicate with each other directly or indirectly.

In various embodiments, all of the components illustrated in FIG. 5, including computing device 110, measurement device 150, water management system 180, and oxidizer generator 120 are configured to communicate directly with each other and/or over network 130 via wired or wireless communication links, or a combination of the two. In various embodiments, each of computing device 110, measurement device 150, water management system 180, and oxidizer generator 120 include one or more communication devices. In various embodiments communication devices comprise any device for communicating over a wired and/or wireless communication channel or communication link. In various embodiments, communication devices include one or more of the following: transceivers, transmitters, receivers, communication cards, network connectors, network adapters, and integrated circuits. In various embodiments, other types of communication devices are used. In various embodiments, computing devices 110 comprise desktop computers, laptop computers, mobile devices (e.g., smart phones, personal digital assistants, tablet devices, or any other devices that are mobile in nature), and/or other types of computing devices.

In various embodiments, computing device 110, measurement device 150, water management system 180, and oxidizer generator 120 are further equipped with one or more computer storage devices and one or more processing devices that are capable of executing computer program instructions. In various embodiments, computer storage devices are physical, non-transitory mediums. In various embodiments, the one or more storage devices communicate with the one or more processors, and the one or more processors execute any instructions stored on the one or more computer storage devices. In various embodiments, the one or more storage devices may include: i) non-volatile memory, such as, for example, read only memory (ROM) or programmable read only memory (PROM); and/or (ii) volatile memory, such as, for example, random access memory (RAM), dynamic RAM (DRAM), static RAM (SRAM), etc. In various embodiments, the one or more storage devices comprise (i) non-transitory memory and/or (ii) transitory memory. In various embodiments, the one or more processors include one or more central processing units (CPUs), controllers, microprocessors, digital signal processors, and/or computational circuits.

Embodiments or aspects of the systems described herein may include a computer program product accessible from a computer-usable or computer-readable medium providing program code for use by or in connection with a computer or any instruction execution system. A computer-usable or computer-readable medium may include any apparatus that stores, communicates, propagates, or transports the program for use by or in connection with the instruction execution system, apparatus, or device. The medium can be a magnetic, optical, electronic, electromagnetic, infrared, or semiconductor system (or apparatus or device) or a propagation medium. The medium may include a computer-readable storage medium, such as a semiconductor or a solid-state memory, a magnetic tape, a removable computer diskette, a random-access memory (RAM), a read-only memory (ROM), a rigid magnetic disk, and an optical disk.

In various embodiments, water management system 180 includes any system, device, and/or apparatus that produces, generates, stores, manages, and/or distributes drinking water and/or other types of water. For example, measurement device 150 can be incorporated into a water management system 180 that produces or generates liquid water by extracting water vapor from ambient air or atmospheric air. In various embodiments, measurement device 150 is utilized in connection with various of the systems, methods, and apparatuses described in: (i) U.S. patent application Ser. No. 15/482,104 filed on Apr. 7, 2017 (U.S. Patent Publication No. 2017-0294876) entitled "SOLAR THERMAL UNIT"; (ii) U.S. patent application Ser. No. 15/600,046 filed on May 19, 2017 (U.S. Patent Publication No. 2018-0043295) entitled "SYSTEMS AND METHODS FOR WATER EXTRACTION CONTROL"; (iii) International Patent App. No. PCT/US18/42098 filed on Jul. 13, 2018 (PCT Patent Publication No. WO/2019/014599) entitled "SYSTEMS FOR CONTROLLED TREATMENT OF WATER WITH OZONE AND RELATED METHODS THEREFOR"; and/or (iv) International Patent App. No. PCT/US15/61921 filed on Nov. 20, 2017 (PCT Patent Publication No. WO/2016/081863) entitled "SYSTEMS AND METHODS FOR GENERATING LIQUID WATER FROM AIR." Measurement device 150 and/or methods described herein can be used in connection with other types of water management systems, as well.

In various embodiments, oxidizer generator 120 is any device or apparatus that is configured to generate and/or apply oxidizing compounds 165 to test fluid 160. In some embodiments (e.g., such as those in which test fluid 160 comprises water), oxidizer generator 120 includes an ozone generator configured to generate and apply or otherwise communicate ozone to the test fluid for the purpose of sterilization. The oxidizer generator 120 can additionally, or alternatively, be configured to generate and/or apply other types of oxidizing compounds 165 to test fluid, including any of the oxidizing compounds 165 mentioned in this disclosure. In certain embodiments, measurements taken by the measurement device 150 can be used to control (e.g., to increase or decrease) the concentration of the oxidizing compounds 165 in test fluid 160. In various embodiments, the oxidizer generator 120 is integrated with water management system 180 to control the concentration of oxidizing compounds 165 in test fluids 160 that include water. For example, in oxidizer measurement system 400, test fluid 160 can be water, and oxidizing compounds 165 (e.g. ozone) can be applied to the water in order to sanitize the water and make it safe for consumption. Measurement device 150 described herein can be configured to measure and control the concentration of oxidizing compounds 165 in the water to ensure that a sufficient amount of oxidizing compounds 165 has been applied to disinfect or sterilize the water and/or to ensure that the water is potable and safe for consumption.

In various embodiments, the control function of measurement device 150 is implemented using one or more processors (e.g., one or more microcontrollers) integrated into measurement device 150 and/or water management system 180. In various embodiments, the control function activates the oxidizer generator 120 if the voltage indicating the oxidizer or ozone concentration measurement reaches a first specified threshold (e.g., indicating that ozone should be applied to reduce the concentration of microbial life in the water), and deactivates the oxidizer generator 120 if the voltage indicating the oxidizer or ozone concentration measurement reaches a second specified threshold (e.g., indicating the current concentration of ozone is sufficient and/or that the water is safe for consumption).

In various embodiments, in response to reaching the second threshold, the control function implements a timeout (e.g., 5 minutes, 10 minutes, 15 minutes, or 1 hour) during which measurement device 150 does not take measurements and oxidizer generator 120 does not apply oxidizing compounds 165. In various embodiments, the control function can be configured to execute a closed loop control technique, in which measurement device 150 will cause the oxidizer generator 120 to apply or otherwise communicate ozone to the test fluid in order to maintain a predefined ozone voltage measurement, and will cut off power to measurement device 150 and/or oxidizer generator 120 when the voltage is registered as sufficient (e.g., when the voltage reaches the second threshold).

In various embodiments, computing device 110 is configured to access measurement device 150, oxidizer generator 120, and/or water management system 180 to monitor and/or control various aspects of oxidizer measurement system 500. For example, computing device 110 can be configured to review measurements and other data generated by measurement device 150. Computing device 110 also can be configured to transmit commands to measurement device 150, oxidizer generator 120, and/or water management system 180 for switching between potentiometric and chronopotentiometric modes, executing the self-cleaning function, managing the control functions, adjusting concentrations of oxidizing compounds 165 in test fluid 160, and/or performing other related functions. Computing device 110 can be operated by an administrator or other individual who is associated with managing measurement device 150 and/or water management system 180.

The embodiments described in this disclosure can be combined in various ways. Any aspect or feature that is described for one embodiment can be incorporated into any other embodiment mentioned in this disclosure. Moreover, any of the embodiments described herein may be hardware-based, may be software-based, or, preferably, may comprise a mixture of both hardware and software elements. Thus, while the description herein may describe certain embodiments, features, or components as being implemented in software or hardware, it should be recognized that any embodiment, feature, or component that is described in the present application may be implemented in hardware and/or software.

Methods of Measuring Oxidizing Compounds in Test Fluid

Figure 6:
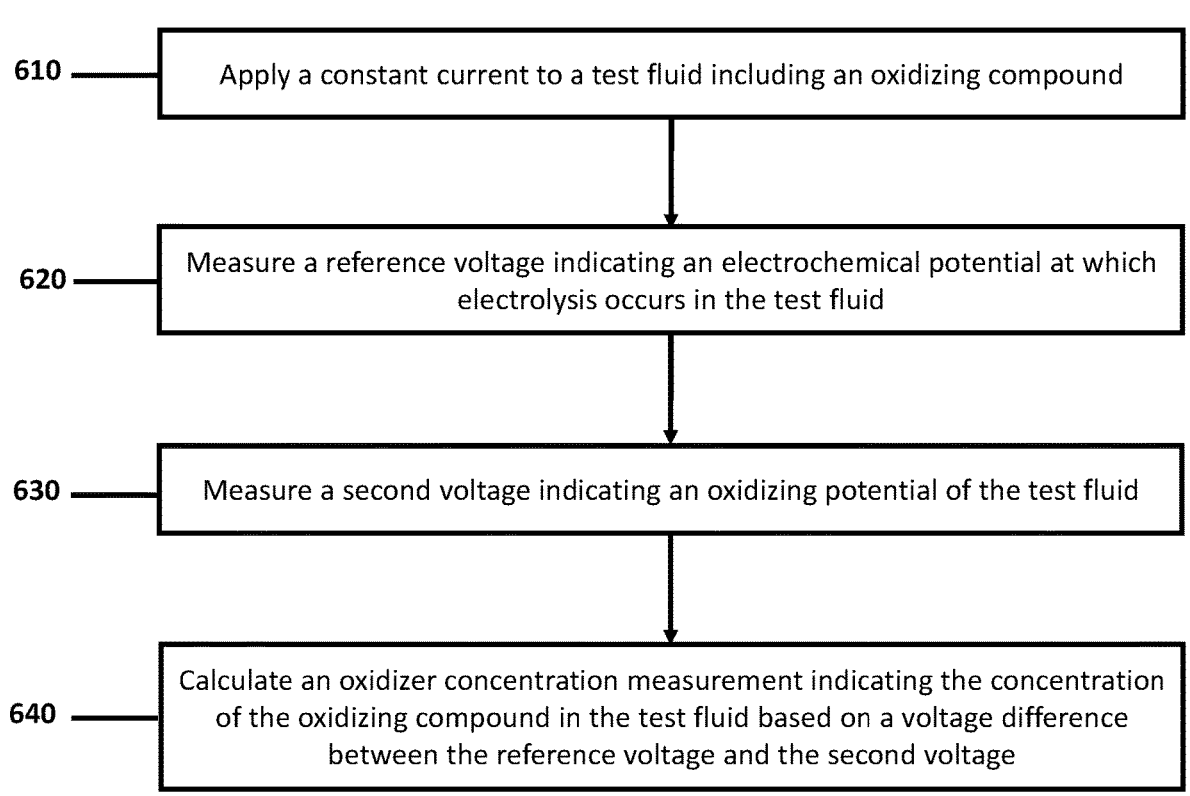
FIG. 6 illustrates a flow chart of an exemplary method in accordance with certain embodiments.
Figure 7:
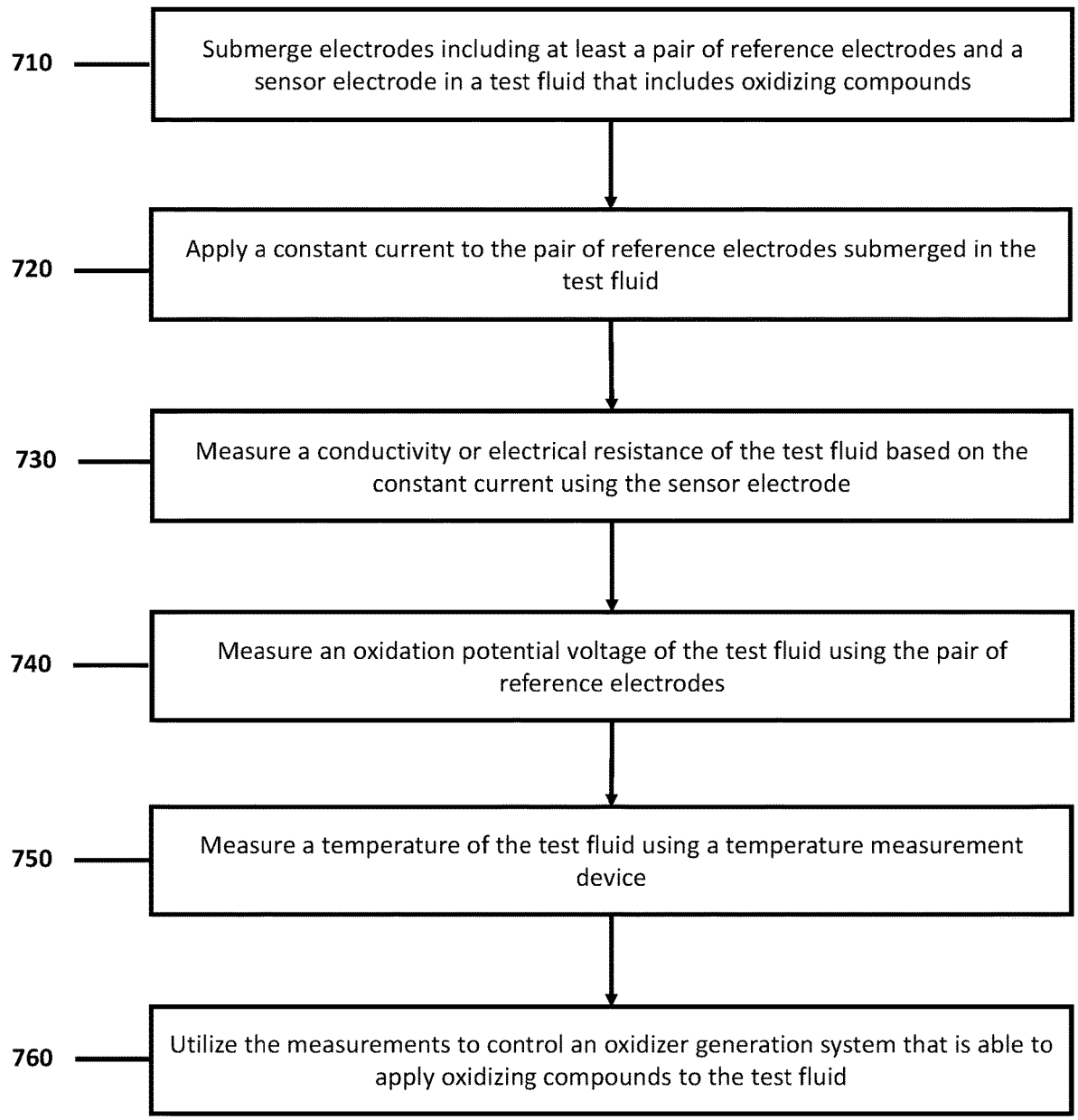
FIG. 7 illustrates a flow chart of a second exemplary method in accordance with certain embodiments.
Figure 8:
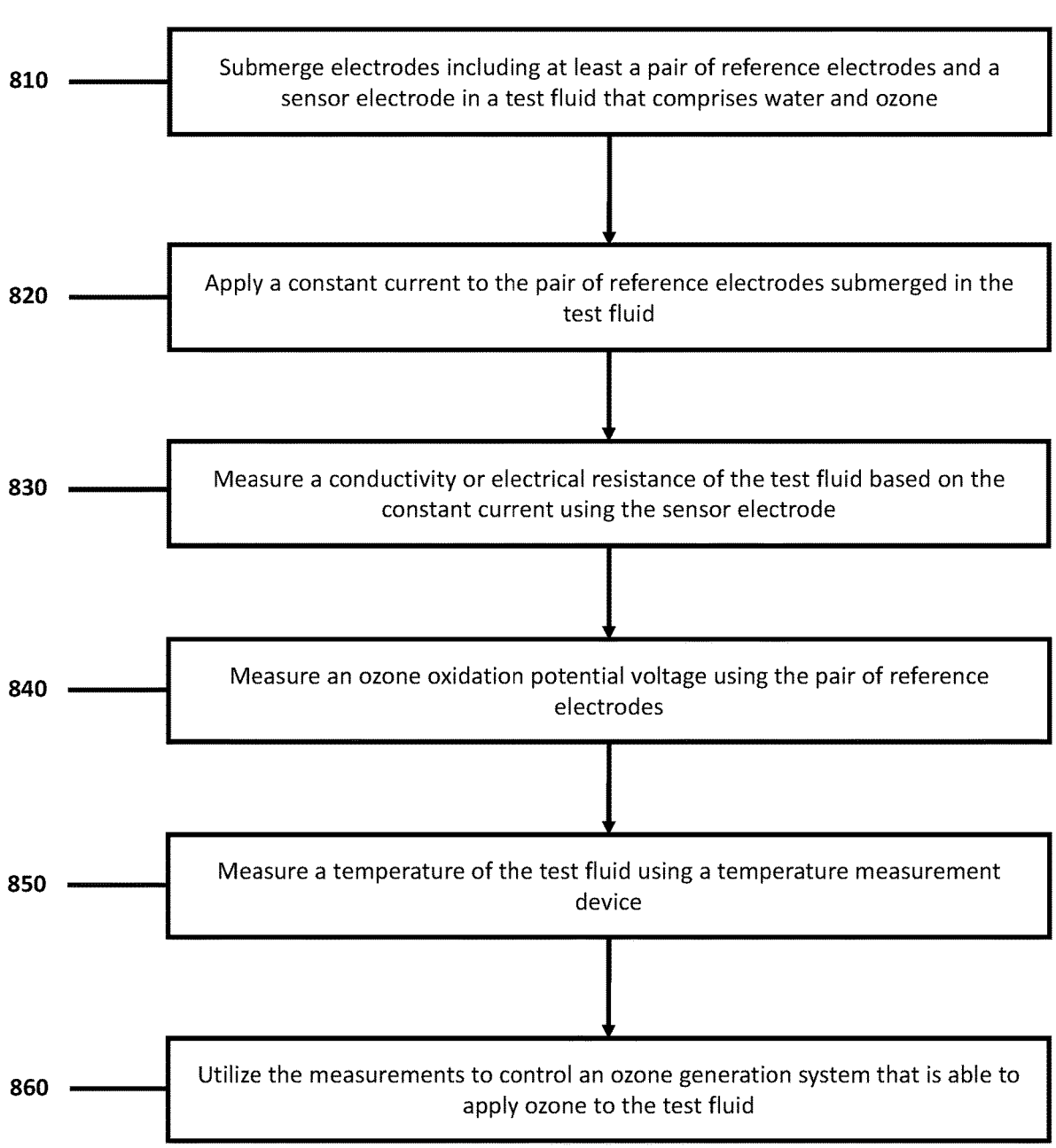
FIG. 8 is a flow chart of a third exemplary method in accordance with certain embodiments.

FIGS. 6-8 illustrate flow charts for exemplary methods 600, 700, and 800, respectively, according to certain embodiments. Methods 600, 700, and 800 are merely exemplary and are not limited to the embodiments presented herein. Methods 600, 700, and 800 can be employed in many different embodiments or examples not specifically depicted or described herein. In some embodiments, the activities of methods 600, 700, and 800 are performed in the order presented. In other embodiments, the activities of methods 600, 700, and 800 are performed in any suitable order. In still other embodiments, one or more of the activities of methods 600, 700, and 800 are combined or skipped. In various embodiments, system 500 (FIG. 5) and/or measurement device 150 (FIGS. 1 and 2) are used suitable to perform methods 600, 700, 800 and/or one or more of the activities of methods 600, 700, and 800. In these or other embodiments, one or more of the activities of methods 600, 700, and 800 are implemented as one or more computer instructions configured to run one or more processors and configured to be stored at one or more non-transitory storage devices. Such non-transitory memory storage devices can be part of system 500 (FIG. 5), measurement device 150 (FIGS. 1 and 2) and/or control board 300 (FIG. 3). The processor(s) can be similar or identical to the processor(s) described above with respect to system 500 (FIG. 5).

FIG. 6 is a flow chart of an exemplary method 600 in accordance with certain embodiments. In various embodiments, method 600 comprises activity 610 of applying a constant current to a test fluid including an oxidizing compound. In various embodiments, method 600 further comprises activity 620 of measuring a reference voltage indicating an electrochemical potential at which electrolysis occurs in the test fluid. In various embodiments, method 600 further comprises activity 630 of measuring a second voltage indicating an oxidizing potential of the test fluid. In various embodiments, method 600 further comprises activity 640 of calculating an oxidizer concentration measurement indicating the concentration of the oxidizing compound in the test fluid based on a voltage difference between the reference voltage and the second voltage. As an example, one of or both of system 500 in FIG. 5 and control board 300 in FIG. 3 can be used to perform some or all of one or more of activities 610, 620, 630, and 640.

FIG. 7 is a flow chart of a second exemplary method 700 in accordance with certain embodiments. In various embodiments, method 700 comprises activity 710 of submerging electrodes, including at least a pair of reference electrodes and a sensor electrode in a test fluid that includes oxidizing compounds. In various embodiments, method 700 further comprises activity 720 of applying a constant current to the pair of reference electrodes submerged in the test fluid. In various embodiments, method 700 further comprises an activity 730 of measuring a conductivity or electrical resistance of the test fluid based on the constant current using the sensor electrode. In various embodiments, method 700 further comprises activity 740 of measuring an oxidation potential voltage of the test fluid using the pair of reference electrodes. In various embodiments, method 700 further comprises activity 750 of measuring a temperature of the test fluid using a temperature measurement component. In various embodiments, method 700 further comprises activity 760 of using the measurements to control an oxidizer generation system that is able to apply oxidizing compounds to the test fluid. As an example, one of or both of system 500 in FIG. 5 and control board 300 in FIG. 3 can be used to perform some or all of one or more of activities 710, 720, 730, 740, 750, and 760.

FIG. 8 is a flow chart of a third exemplary method 800 in accordance with certain embodiments. In various embodiments, method 800 comprises activity 810 of submerging electrodes, including at least a pair of reference electrodes and a sensor electrode in a test fluid that comprises water and ozone. In various embodiments, method 800 further comprises activity 820 of applying a constant current to the pair of reference electrodes submerged in the test fluid. In various embodiments, method 800 further comprises activity 830 of measuring, using the sensor electrode, a conductivity or electrical resistance of the test fluid based on the constant current. In various embodiments, method 800 further comprises an activity 840 of measuring, using the pair of reference electrodes, an ozone oxidation potential voltage. In various embodiments, method 800 further comprises activity 850 of measuring, using a temperature measurement component, a temperature of the test fluid. In various embodiments method 800 further comprises activity 860 of utilizing the measurements to control an ozone generation system that is able to apply or otherwise communicate ozone to the test fluid. As an example, one of or both of system 500 in FIG. 5 and control board 300 in FIG. 3 can be used to perform some or all of one or more of activities 810, 820, 830, 840, 850, and 860.

Although the disclosure has been made with reference to specific embodiments, it will be understood by those skilled in the art that various changes may be made without departing from the spirit or scope of the disclosure. Accordingly, the disclosure of embodiments is intended to be illustrative of the scope of the disclosure and is not intended to be limiting. It is intended that the scope of the disclosure shall be limited only to the extent required by the appended claims. For example, to one of ordinary skill in the art, it will be readily apparent that any element of FIGS. 1-8 may be modified, and that the foregoing discussion of certain of these embodiments does not necessarily represent a complete description of all possible embodiments. For example, one or more of the procedures, processes, and/or activities of FIGS. 6-8 may include different procedures, processes, and/or activities and be performed by many different modules and/or components, in many different orders. As another example, the elements of the measurement device 150 and oxidizer measurement system 500 can be interchanged or otherwise modified.

All elements claimed in any particular claim are essential to the embodiment claimed in that particular claim. Consequently, replacement of one or more claimed elements constitutes reconstruction and not repair. Additionally, benefits, other advantages, and solutions to problems have been described with regard to specific embodiments. The benefits, advantages, solutions to problems, and any element or elements that may cause any benefit, advantage, and/or solution to occur or become more pronounced, however, are not to be construed as critical, required, or essential features or elements of any or all of the claims, unless such benefits, advantages, solutions, and/or elements are stated in such claim.

Moreover, embodiments and limitations disclosed herein are not dedicated to the public under the doctrine of dedication if the embodiments and/or limitations: (1) are not expressly claimed in the claims; and (2) are, or potentially are, equivalents of express elements and/or limitations in the claims under the doctrine of equivalents.

What is claimed is:

1. A water testing and measuring system, comprising:
   a water generator configured to generate water by extracting water vapor from ambient air;
   a compound generator configured to apply a compound to the water generated by the water generator;
   a measurement device comprising:
      a first and second reference electrode assembled on a first circuit as a reference pair; and
      a first sensor electrode;
   and
   a microcontroller configured to:
      apply a current to the first and second reference electrodes on the first circuit to electrolyze the water generated by the water generator, wherein the current is applied to the first and second reference electrodes but not to the first sensor electrode;
      measure a reference voltage between the reference pair of the first circuit indicating a reference potential of electrolysis of the water generated by the water generator;
      measure a first sense voltage between the first sensor electrode and the first reference electrode indicating a potential of the water generated by the water generator;
      receive the reference voltage and the first sense voltage;
      determine a concentration measurement in the water generated by the water generator based on a voltage difference between the reference voltage and the first sense voltage; and
      control the compound generator to apply the compound to the water generated by the water generator based on the concentration measurement to ensure that the water generated by the water generator is tested safe.

2. The water testing and measuring system of claim 1, wherein the first sense voltage indicating the potential of the water relates to: a pH potential, or an ion concentration chemical potential of the water generated by the water generator.

3. The water testing and measuring system of claim 1, wherein the microcontroller is further configured to control the compound generator by increasing or decreasing the concentration of the compound in the water generated by the water generator based on the concentration measurement.

4. The water testing and measuring system of claim 1, wherein the microcontroller is further configured to control the compound generator by activating the compound generator if the concentration measurement reaches a first specified threshold and deactivating the compound generator if the concentration measurement reaches a second specified threshold.

5. The water testing and measuring system of claim 4, wherein the microcontroller is further configured to determine the first specified threshold indicates that the compound should be applied to reduce a concentration of microbial life in the water generated by the water generator, and the second specified threshold indicates a concentration of the compound in the water generated by the water generator is sufficient.

6. The water testing and measuring system of claim 4, wherein the microcontroller is further configured to, in response to reaching the second specified threshold, implement a timeout period during which the measurement device does not measure the reference voltage or the first sense voltage.

7. The water testing and measuring system of claim 6, wherein a duration of the timeout period is about one hour or less.

8. The water testing and measuring system of claim 1, wherein the microcontroller is further configured to control the compound generator in a closed loop control technique in which the microcontroller is configured to:
   activate the compound generator to maintain the concentration measurement at a first concentration measurement threshold; and
   deactivate, in response to reaching a second concentration measurement threshold, one or more of the measurement device and the compound generator.

9. The water testing and measuring system of claim 1, wherein the microcontroller is further configured to:
   compare the concentration measurement to a library of pre-stored conditions; and
   control the compound generator based on the comparison of the concentration measurement to the library of the pre-stored conditions.

10. The water testing and measuring system of claim 1, wherein the microcontroller is further configured to provide a constant current of about 1 µA to about 10 µA of current to the first circuit.

11. The water testing and measuring system of claim 1, wherein the water generator, the compound generator, the microcontroller and the measurement device are in communication with each other over a network.

12. The water testing and measuring system of claim 1, further comprising a computing device in communication with the measurement device, the compound generator and the water generator; the computing device being configured to:
   monitor data measured by the measurement device; and
   transmit control commands to the measurement device, the compound generator and the water generator.

13. The water testing and measuring system of claim 1, wherein the first reference electrode, the second reference electrode and the first sensor electrode are each constructed of a similar metal that is stable under the conditions applied to the measurement device when submerged in the water generated by the water generator.

14. The water testing and measuring system of claim 1, wherein the first reference electrode, the second reference electrode and the first sensor electrode are each constructed of a similar metal.

15. The water testing and measuring system of claim 1, wherein the first reference electrode, the second reference electrode and the first sensor electrode are each constructed of a metal, or a glass-like carbon.

16. The water testing and measuring system of claim 1, wherein the measurement device further comprises a temperature measurement component that is configured to measure a second sense voltage indicating a temperature of the water generated by the water generator.

17. The water testing and measuring system of claim 1, wherein the measurement device is configured to operate in a reverse polarization mode during which a constant current applied to the water is reversed to produce a reaction on the first reference electrode and the second reference electrode.

18. The water testing and measuring system of claim 1, wherein the measurement device further comprises a third reference electrode that is paired on a second circuit with the first sensor electrode.

19. The water testing and measuring system of claim 1, wherein the microcontroller is further configured to:
   short the first reference electrode and the first sensor electrode to an electrical ground, thereby applying a reducing potential to purge a surface of the first reference electrode and a surface of the first sensor electrode of the compound;
   cease an electrical current to the first sensor electrode such that current is applied to the first and second reference electrodes but not to the first sensor electrode.

20. The water testing and measuring system of claim 1, wherein the first sensor electrode, after being shorted and/or purged of all or substantially all oxidizing compounds on its surface, may begin again to be oxidized by the compound present in the water.

21. The water testing and measuring system of claim 20, wherein the microcontroller is further configured to determine the concentration measurement in the water based on a maximum of the first sense voltage and a time to reach the maximum of the first sense voltage.

22. The water testing and measuring system of claim 20, wherein the microcontroller is further configured to determine a concentration measurement of microbes in the water based on a slope of the first sense voltage versus time after purging the surface of the first sensor electrode indicating a recovery of the first sense voltage.

\* \* \* \* \*